(12) United States Patent
Bell et al.

(10) Patent No.: US 11,744,530 B2
(45) Date of Patent: Sep. 5, 2023

(54) RADIOGRAPHIC DENTAL JIGS AND ASSOCIATED METHODS

(71) Applicants: Patrick C. Bell, La Crosse, WI (US); Leo J. Malin, La Crosse, WI (US); Thomas J. Arendt, Norwalk, WI (US)

(72) Inventors: Patrick C. Bell, La Crosse, WI (US); Leo J. Malin, La Crosse, WI (US); Thomas J. Arendt, Norwalk, WI (US)

( * ) Notice: Subject to any disclaimer, the term of this patent is extended or adjusted under 35 U.S.C. 154(b) by 597 days.

(21) Appl. No.: 17/021,677

(22) Filed: Sep. 15, 2020

(65) Prior Publication Data

US 2022/0079533 A1    Mar. 17, 2022

(51) Int. Cl.
*A61B 6/14* (2006.01)
*A61B 90/16* (2016.01)
(Continued)

(52) U.S. Cl.
CPC .............. *A61B 6/145* (2013.01); *A61B 90/16* (2016.02); *A61B 90/36* (2016.02); *A61B 90/39* (2016.02);
(Continued)

(58) Field of Classification Search
CPC ...... A61B 2090/363; A61B 2090/3966; A61B 2090/3983; A61B 6/145; A61B 90/16;
(Continued)

(56) References Cited

U.S. PATENT DOCUMENTS

| 5,415,546 A | 5/1995 | Cox, Sr. |
| 6,073,044 A | 6/2000 | Fitzpatrick et al. |

(Continued)

FOREIGN PATENT DOCUMENTS

| EP | 1599148 B1 | 4/2011 |
| KR | 101594497 B1 | 2/2016 |

(Continued)

OTHER PUBLICATIONS

International Search Report, issued in connection with PCT/US2021/016917, dated Mar. 29, 2021, 8 pages.
(Continued)

*Primary Examiner* — Mark R Gaworecki
(74) *Attorney, Agent, or Firm* — bobiharter.com; Robert J. Harter

(57) ABSTRACT

Example radiographic dental jigs include a generally vertical post traversed by a generally horizontal beam to create a cross that can be used for marking a dental patient's midline (vertical line centered between the eyes), incisal edge plane, and forward lip position. The jig is radiographically scanned along with multiple fiducial markers on the patient's jaw to generate a first scan result. In some examples, physical models of the patient's jaws are also scanned to generate upper and lower jaw images. The upper and lower jaw images are shifted to coincide with the first scan result. Portions of the first scan result, including an image of the dental jig, are superimposed onto the properly shifted upper and lower jaw images to create a composite image. The composite image shows the dental jig in proper relation to the patient's upper and lower jaws, thereby rendering a conventional stick bite virtually obsolete.

20 Claims, 23 Drawing Sheets

(51) Int. Cl.
    *A61C 8/00* (2006.01)
    *A61C 9/00* (2006.01)
    *A61C 13/00* (2006.01)
    *A61B 90/00* (2016.01)
(52) U.S. Cl.
    CPC .......... *A61C 8/0018* (2013.01); *A61C 8/0028* (2013.01); *A61C 9/0046* (2013.01); *A61C 9/0053* (2013.01); *A61C 13/0004* (2013.01); *A61B 2090/363* (2016.02); *A61B 2090/3966* (2016.02); *A61B 2090/3983* (2016.02)
(58) Field of Classification Search
    CPC ..... A61B 90/36; A61B 90/39; A61C 13/0004; A61C 8/0018; A61C 8/0028; A61C 9/0046; A61C 9/0053
    See application file for complete search history.

(56) References Cited

U.S. PATENT DOCUMENTS

| | | | |
|---|---|---|---|
| 6,096,048 | A | 8/2000 | Howard, III et al. |
| 6,102,914 | A | 8/2000 | Bulstra et al. |
| 6,333,971 | B2 | 12/2001 | McCrory et al. |
| 6,499,488 | B1 | 12/2002 | Hunter et al. |
| 6,565,573 | B1 | 5/2003 | Ferrante et al. |
| 6,582,931 | B1 | 6/2003 | Kois et al. |
| 6,866,666 | B1 | 3/2005 | Sinnott et al. |
| 6,942,667 | B1 | 9/2005 | Song |
| D528,211 | S | 9/2006 | Solar et al. |
| 7,601,000 | B1 | 10/2009 | Hammond |
| 7,787,934 | B2 | 8/2010 | Mazzocchi et al. |
| 8,170,645 | B2 | 5/2012 | Solar et al. |
| 8,172,573 | B2 | 5/2012 | Sonenfeld et al. |
| 8,185,184 | B2 | 5/2012 | Solar et al. |
| 8,348,669 | B1 * | 1/2013 | Schmitt ............... A61C 9/0046 433/213 |
| 8,808,000 | B2 | 8/2014 | Salcedo et al. |
| 9,265,590 | B2 | 2/2016 | Zagorchev et al. |
| 9,554,869 | B1 | 1/2017 | Huang et al. |
| 9,877,810 | B2 | 1/2018 | Mozes et al. |
| 9,955,929 | B2 | 5/2018 | Huang et al. |
| 10,022,104 | B2 | 7/2018 | Sell et al. |
| 10,952,814 | B2 | 3/2021 | Kim et al. |
| 2001/0004395 | A1 | 6/2001 | McCrory et al. |
| 2002/0094509 | A1 | 7/2002 | Durbin |
| 2004/0030236 | A1 | 2/2004 | Mazzocchi et al. |
| 2004/0030237 | A1 | 2/2004 | Lee et al. |
| 2004/0167393 | A1 | 8/2004 | Solar et al. |
| 2006/0121409 | A1 | 6/2006 | Olivier |
| 2006/0241406 | A1 | 10/2006 | Noujeim |
| 2008/0234532 | A1 | 9/2008 | De Langen et al. |
| 2013/0172731 | A1 | 7/2013 | Gole |
| 2013/0337400 | A1 | 12/2013 | Yi et al. |
| 2014/0270067 | A1 | 9/2014 | Clark |
| 2014/0379356 | A1 | 12/2014 | Sachdeva |
| 2018/0333231 | A1 | 11/2018 | Somasundaram et al. |
| 2019/0151046 | A1 | 5/2019 | Kim et al. |

FOREIGN PATENT DOCUMENTS

| | | |
|---|---|---|
| WO | WO2007019113 A2 | 2/2007 |
| WO | WO 2019151923 A1 | 8/2019 |

OTHER PUBLICATIONS

International Search Report, issued in connection with PCT/US2021/012871, dated Mar. 25, 2021, 10 pages.

International Search Report, issued in connection with PCT/US2021/012791, dated Mar. 26, 2021, 10 pages.

Tab2, Summary of Safety and Effectiveness, 510(k) Summary per 21 CFR 807.92(c), Self-Drilling Radiographic Marker, Jacksonville, Florida, 4 pages, published May 13, 2004.

Unitek, TAD Temporary Anchorage Device, 3M Company, St. Paul, MN; www.3m.com/3M/en_US/company-us/all-3m-products/~/Unitek-TADs/?N=5002385+3290412411&preselect=8710666&rt=rud; website; one page plus hyperlinks to related information; publically available and retrieved for viewing on Feb. 4, 2020.

Dentsply, Dentsply Sirona Company, Salzburg, Austria; www.dentsplysirona.com; website; 2 pages plus hyperlinks to various dental tools and software, publically available and retrieved for viewing on Feb. 4, 2020.

Dental Wings, Welcome to Dental Wings, Straumann Group Dental Wings Company, Montreal, Quebec, www.dentalwings.com; website; 2 pages plus hyperlinks to various dental software downloads, publically available and retrieved for viewing on Feb. 4, 2020.

3Shape, We Innovate for Superior Patient Care, 3Shape Company, CopenHagen, Denmark, www.3shape.com website, 2 pages plus hyperlinks, publically available and retrieved for viewing on Feb. 4, 2020.

Exocad, Your Future in Digital Dentistry, exocad GmbH Company, Darmstadt, Hessen, www.exocad.com website, 2 pages plus hyperlinks, publically available and retrieved for viewing on Feb. 4, 2020.

Sha; Medical Device and Diagnostic Industry; Radiopaque Polymer Formulations for Medical Devices; Tilak M. Shah; Los Angeles, CA; 6 pages; Mar. 2000.

Gold Dust; How to Take a Stick Bite Your Lab can Use; Gold Dust Dental Lab; Tempe, AZ; 1 page, Nov. 12, 2015.

Scherer, Michael D.; Presurgical Implant-Site Assessment and Restoratively Driven Digital Planning; Dental Clinics of North America, vol. 58, Issue 3; 35 pages (pp. 561-595); dated Jul. 2014.

* cited by examiner

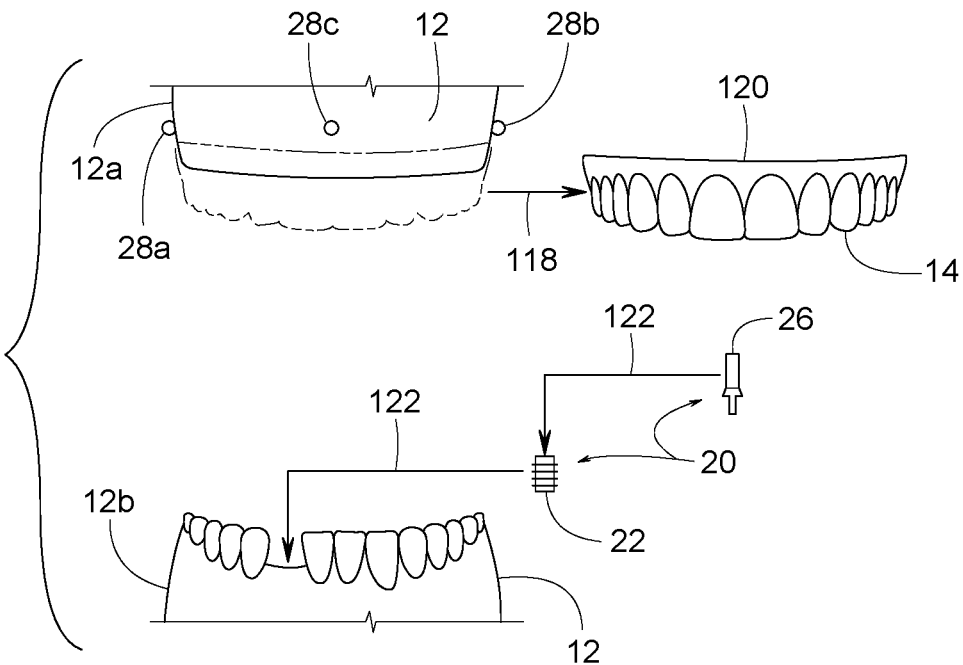
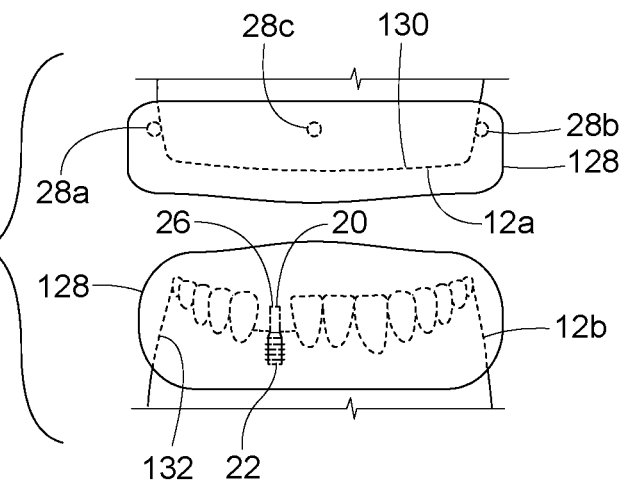
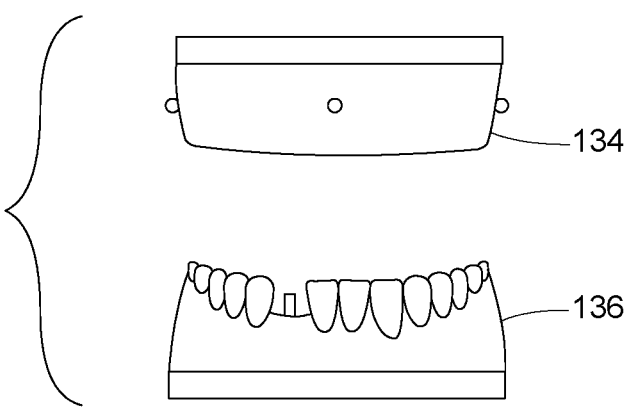

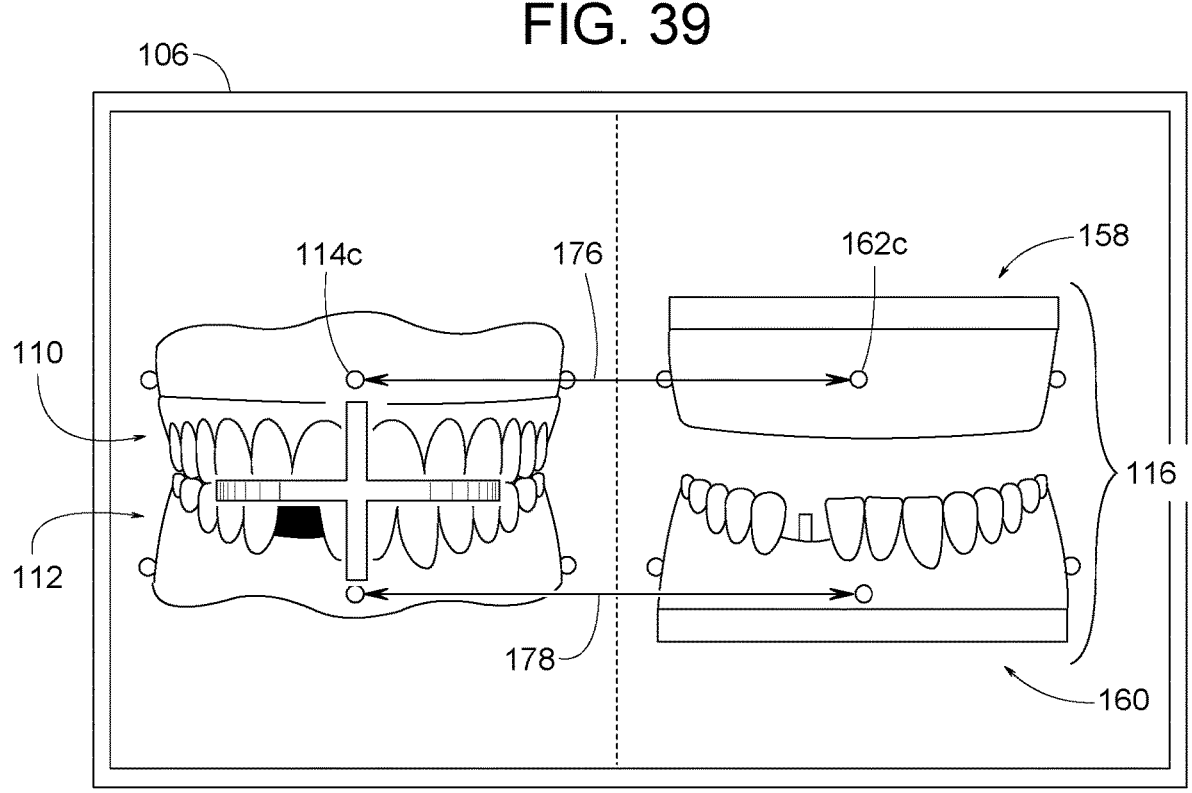
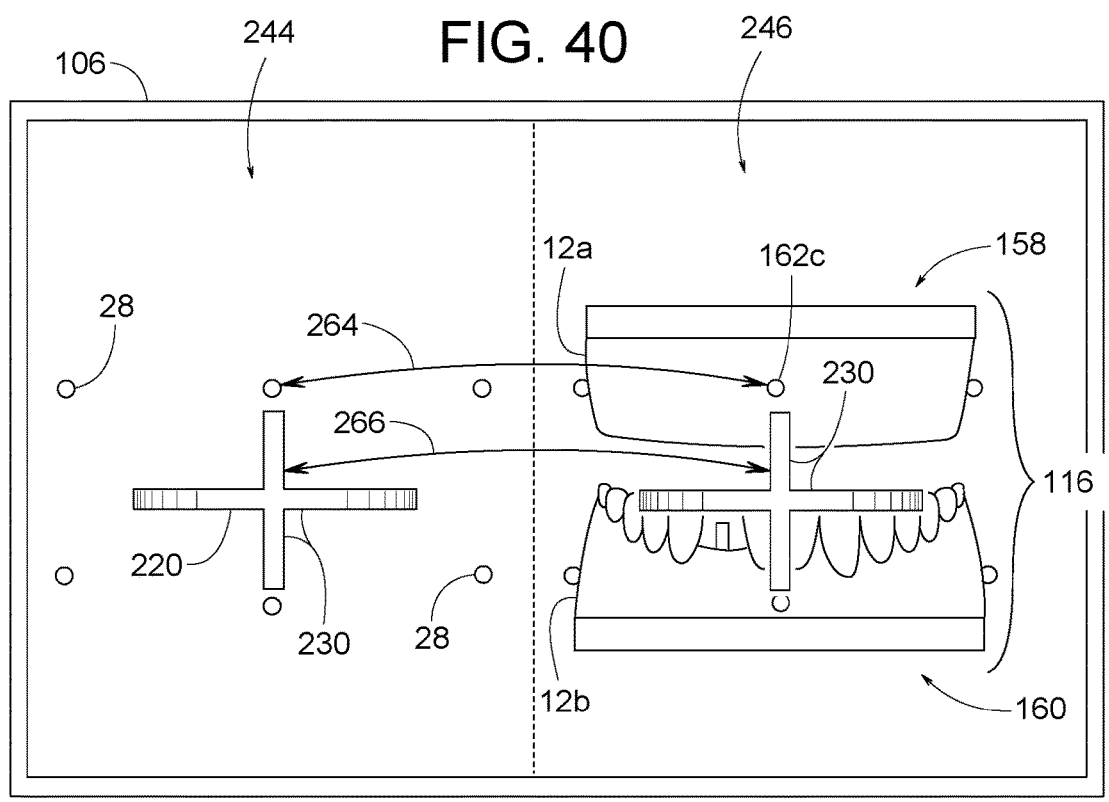

RADIOGRAPHIC DENTAL JIGS AND ASSOCIATED METHODS

FIELD OF THE DISCLOSURE

This patent generally pertains to dentistry and more specifically to radiographic jigs for establishing and/or recording a patient's actual or desired incisal edge plane, midline, and/or a reference location of a patient's lips.

BACKGROUND

A typical jaw of a person or human patient includes a maxilla (upper jaw) and a mandible (lower jaw). Temporamandibular joints (TMJ) allow pivotal and some translational relative movement between the maxilla and mandible, so the person can pivotally open and close their mouth. Both the maxilla and mandible comprise an alveolar bone for supporting teeth. A curved portion of the alveolar bone is known as the alveolar arch, which curves about an oral cavity within the person's mouth. The oral cavity is the space that contains the person's tongue.

Normally, when a person closes their mouth, the teeth in the upper and lower jaws come together in a comfortable engaging relationship known as proper bite registration. Other times, however, malpositioned teeth, missing teeth or interfering dental appliances prevent the jaws from closing in proper bite registration. This can create a number of problems such as stressing the temporamandibular joints, concentrating localized force on certain teeth, and creating a poor visual appearance. Consequently, various dental treatments are used for correcting such problems.

Planning and performing certain dental treatments might first involve creating physical cast models of a patient's upper and lower jaws and analyzing how well the cast models fit together before and after treatment. Some example treatments include installing dentures, repairing dentures, installing implants, applying crowns, jaw surgery, applying braces, and removing teeth.

In some cases, various scanners are used for assisting in the dental treatment process. Some scanners generate a dicom file, which is an acronym for Digital Imaging and Communications in Medicine. Some dicom files have a .dcm file extension.

In some cases, a dental practitioner might create what is known in the industry as a "stick bite." A stick bite can be used as a visual aide to more clearly show the actual location of a patient's incisal edge plane. In some cases, a stick bite is simply a generally horizontal stick embedded or otherwise stuck to some type of impression material or bite registration compound. The patient bites into the impression material, which then holds the stick generally along the patient's incisal edge.

BRIEF DESCRIPTION OF THE DRAWINGS

FIG. 11 is a front view showing example dental appliances being added and removed from the patient as shown in FIG. 2.

FIG. 12 is a front view showing an example method for creating cast models of the patient's jaws after the addition or removal of example dental appliances.

FIG. 13 is a front view of cast models created by the method shown in FIG. 12.

FIG. 39 is a front view similar to FIG. 20 but showing the additional use of the example jig.

FIG. 40 is a front view similar to FIG. 21 but showing the additional use of the example jig.

DETAILED DESCRIPTION

FIGS. 1-27 pertain to a dental scanning method for analyzing jaws of a patient 10 by taking multiple scans of the jaws, and/or models thereof, and then shifting the image of one scan to match that of another. In some examples, fiducial markers are attached to the patient's jaws beforehand to accurately identify and track the relative position of the jaws. The method provides a way for creating a precise image of an upper jaw 12a and a lower jaw 12b in their proper bite registration, even though the resulting image may show an insufficient number of teeth to readily do so. The final, properly shifted image serves as a virtual 3D jaw that can be manipulated and analyzed to aid in various orthodontic and other dental treatments.

Figure 1:
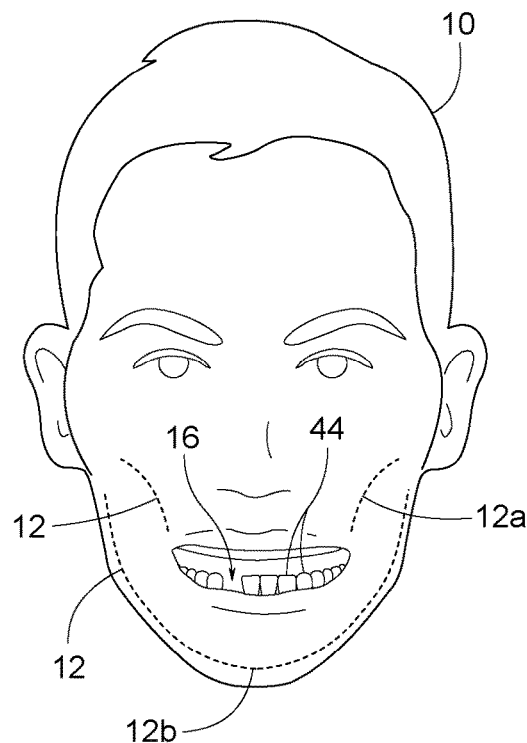
FIG. 1 is a front view of an example patient that has no upper teeth and is missing one lower tooth.
Figure 2:
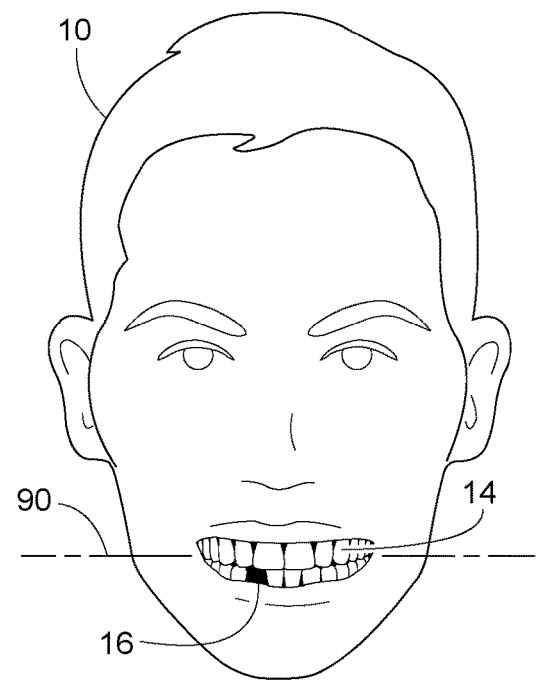
FIG. 2 is a front view of the patient shown in FIG. 1 but with the addition of a poor-fitting upper denture.

The method can be applied to an infinite variety of patients and treatments. Some example treatments include installing dentures, repairing dentures, installing implants, applying crowns, jaw surgery, grinding teeth, shifting teeth, removing teeth, and all other conceivable modifications to the craniofacial complex. For sake of example, the present method can be applied to patient 10, shown in FIGS. 1-3. In this particular example, patient 10 has no upper teeth and is missing a lower tooth, as shown in FIG. 1. Prior to using the method disclosed herein, patient 10 wore an old, poor fitting upper denture 14 and left an area 16 of the missing lower tooth open, as shown in FIG. 2.

Figure 3:
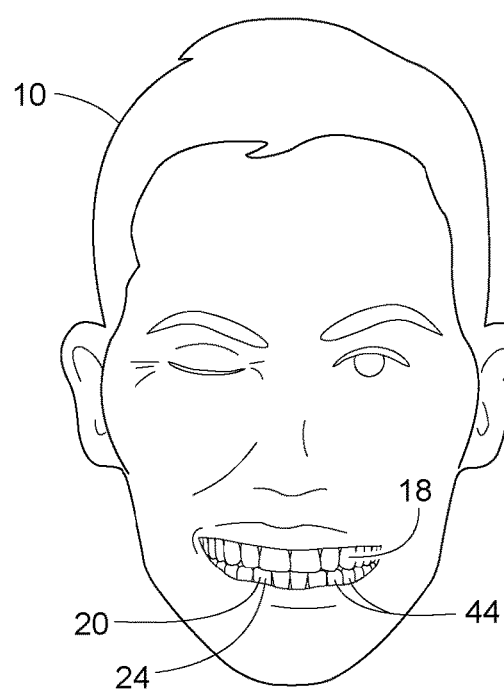
FIG. 3 is a front view of the patient shown in FIG. 1 but with the addition of a new upper denture and an implant replacing the missing lower tooth.

Following treatment, patient 10 is provided with a well fitting upper denture 18 plus an implant 20 to fill the space of the missing tooth, as shown in FIG. 3. The term, "implant" refers to an anchor 22 attached to a jaw bone and/or a crown 24 attached to anchor 22. Some example implants further include a post 26 (e.g., a screw, a rod, a pin, etc.) for fastening crown 24 to anchor 22.

Patient 10 has two jaw members 12 including upper jaw 12a (maxilla) and lower jaw 12b (mandible). The term, "first jaw" refers to either jaw, the maxilla or the mandible. Likewise, the term, "second jaw" refers interchangeably to the maxilla or mandible. FIGS. 4-7, 11 and 12 show the patient's actual jaw members 12, not models thereof. FIGS. 4-7 show jaws 12a and 12b in the condition similar to that shown in FIG. 2, wherein old denture 14 is on upper jaw 12a and space 16 is left empty.

To provide jaw 12a and/or jaw 12b with reference points that help identify the jaws' relative location and orientation in later scanned images of jaws 12a and 12b, some example methods involve installing multiple fiducial markers 28 into an alveolar bone 30 (FIGS. 8 and 9) of jaw 12a and/or 12b. The term, "alveolar bone" refers to the bony structure of either jaw 12a or 12b. The term, "fiducial marker" refers to any item that includes a substantially radiopaque feature.

Figure 25:
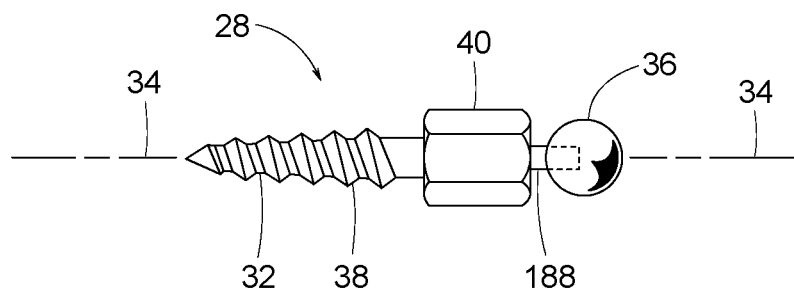
FIG. 25 is a side view of an example fiducial marker constructed in accordance with the teachings disclosed herein.
Figure 26:
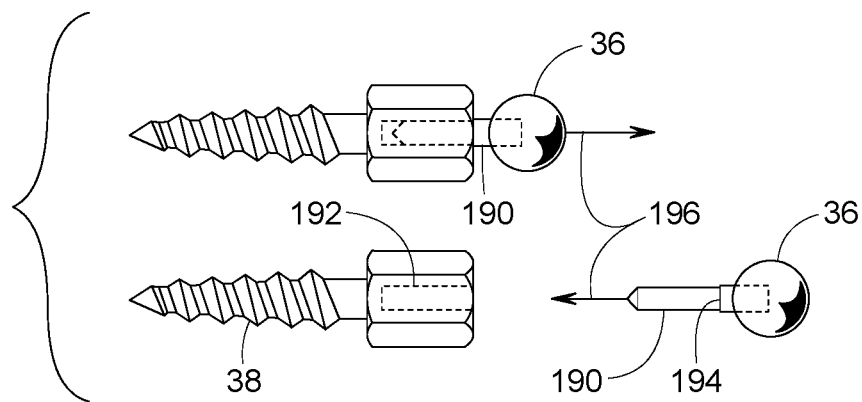
FIG. 26 are side views of another example fiducial marker constructed in accordance with the teachings disclosed herein.
Figure 27:
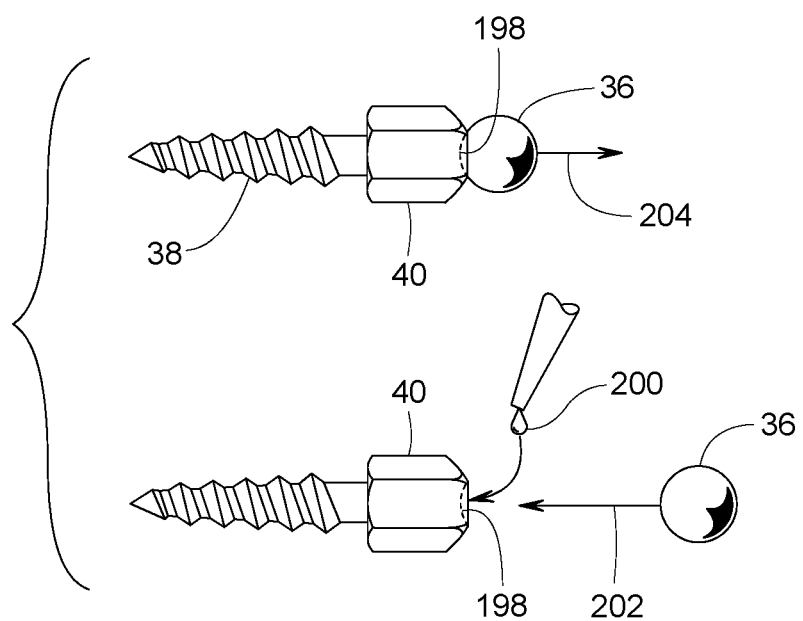
FIG. 27 are side views of yet another example fiducial marker constructed in accordance with the teachings disclosed herein.

Some examples of fiducial marker 28 comprise a shaft 32 extending along a longitudinal axis 34 from a marker body 36. The term, "shaft" refers to any elongate member that is generally cylindrical, tapered and/or threaded. Some examples of shaft 32 include a screw, a straight pin, a tapered pin, a rod, a nail, etc. In the illustrated examples, shaft 32 is a screw 38. The term, "marker body" refers to any structure of any shape that is substantially radiopaque. In some examples, marker body 36 is generally spherical and made of a polymer with 20-70% barium sulfate. In some examples, marker body 36 is overmolded or otherwise attached to a head 40 of screw 38. Some examples of screw 38 are made of a generally noncorrosive material, such as stainless steel, carbide or titanium. Head 40, in some examples, has a tool-mating geometry, so screw 38 can be readily driven into jaw member 12. Various examples of fiducial marker 28 are shown in FIGS. 25-27 and will be described later in more detail.

Figure 4:
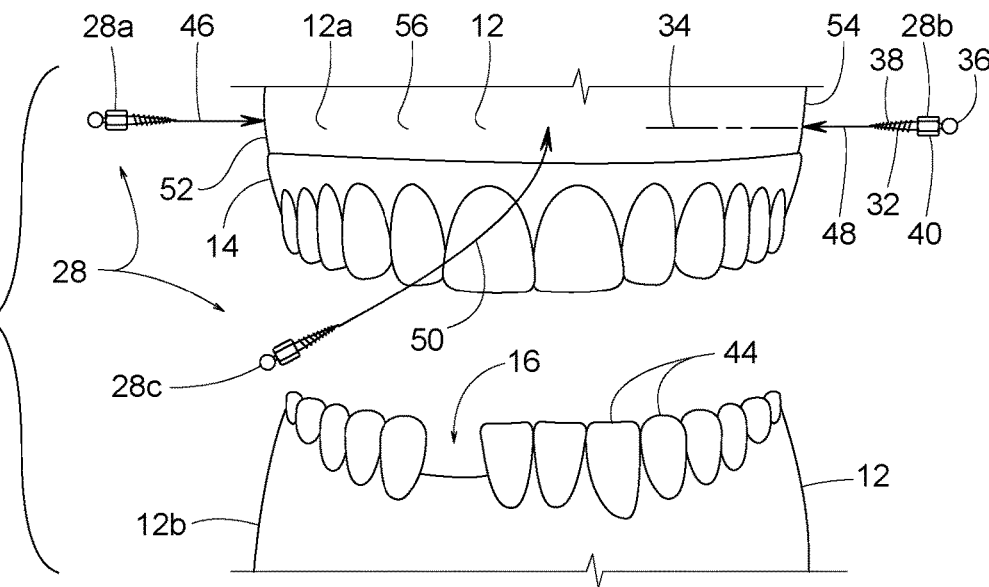
FIG. 4 is a front view of the patient's upper and lower jaws with fiducial markers being installed in the upper jaw, just above the poor-fitting upper denture.
Figure 5:
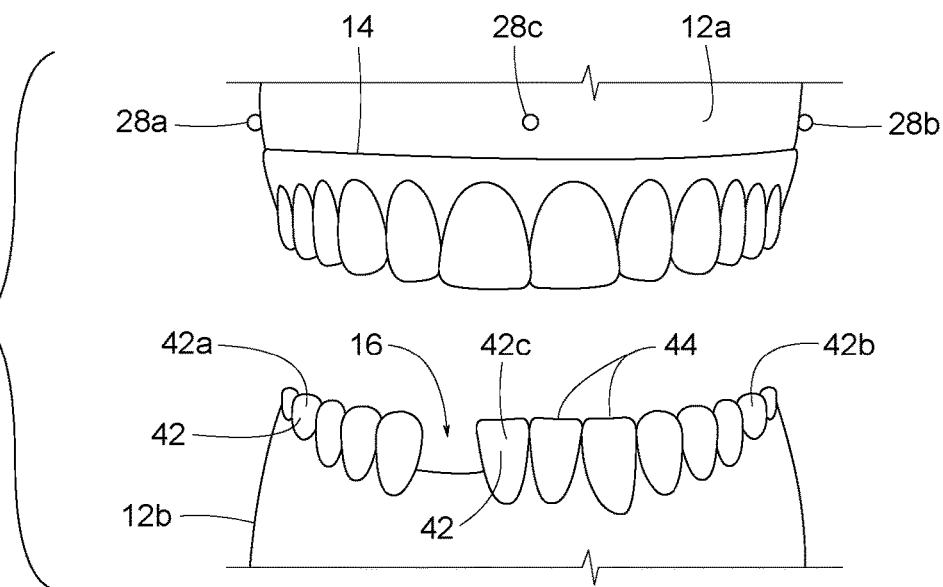
FIG. 5 is a front view similar to FIG. 4 but showing the fiducial markers already installed.

For minimal invasiveness, in some examples, markers 28 are only installed in one of jaw members 12, as shown in FIGS. 4 and 5, and distinct stable features 42 of teeth 44 are used as reference points on the other jaw member 12. Some examples of features 42 include chosen edges, corners, faces, and peaks of individual teeth 44 or a dental appliance supported by one of the jaws 12. More specific examples include a first feature 42a (face of a first chosen tooth), a second feature 42b (face of a second chosen tooth), and a third feature 42c (face of a third chosen tooth).

In the example shown in FIGS. 4 and 5, fiducial markers 28 include a right fiducial marker 28a, a left fiducial marker 28b, and a front fiducial marker 28c. Arrows 46, 48 and 50 respectively represent attaching right fiducial marker 28a to a right portion 52 of first jaw 12a, attaching left fiducial marker 28b to a left portion 54 of first jaw 12a, and attaching front fiducial marker 28c to a front portion 56 of first jaw 12a. FIG. 5 shows markers 28a, 28b and 28c in their installed positions. Such a spread-out arrangement of three markers 28 provides upper jaw 12a with a broad footprint for maximum positional accuracy.

Figure 6:
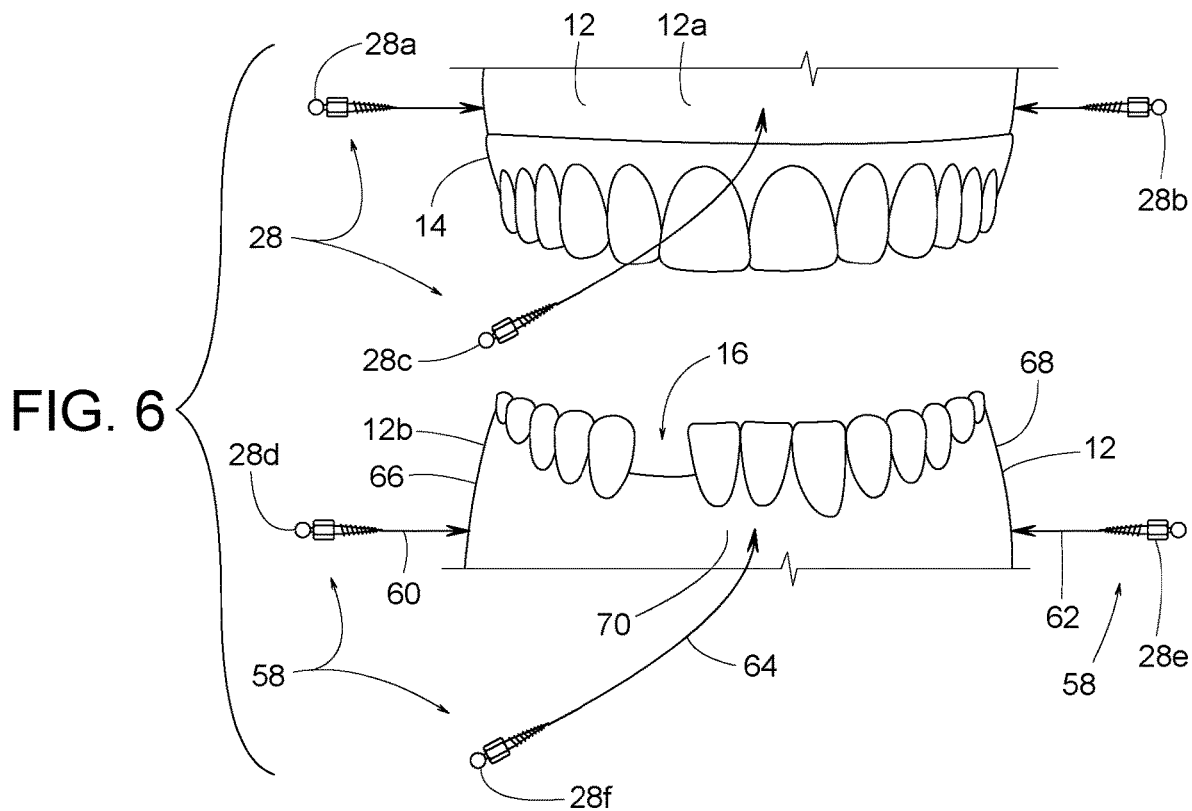
FIG. 6 is a front view similar to FIG. 4 but showing fiducial markers being installed in both the upper and lower jaws.
Figure 7:
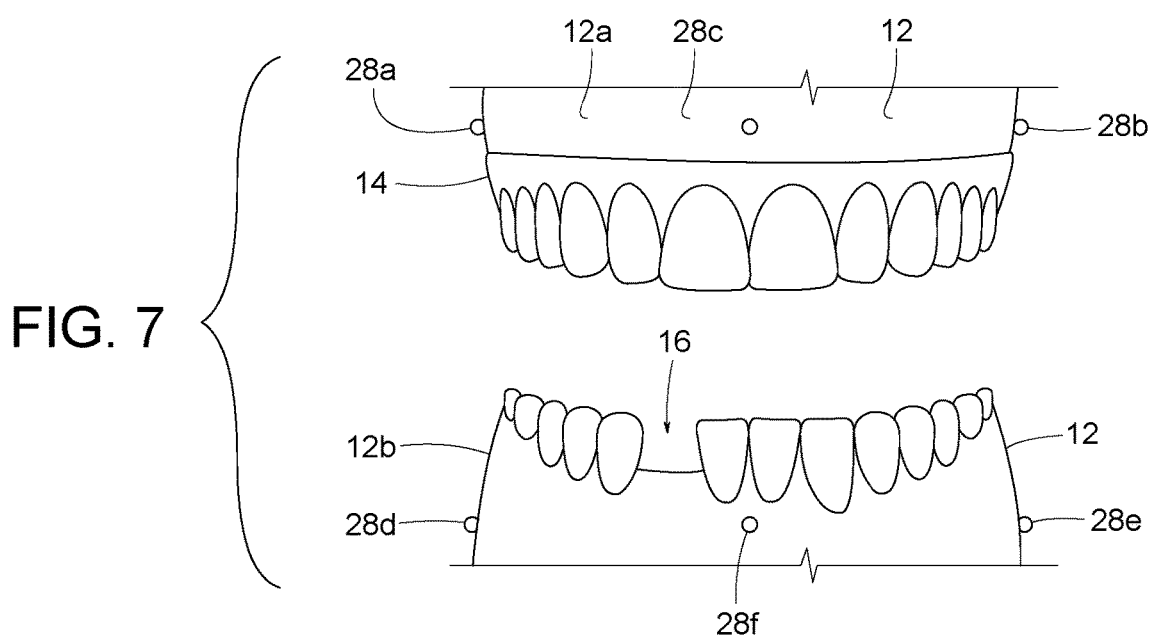
FIG. 7 is a front view similar to FIG. 6 but showing the fiducial markers already installed.

In addition or alternatively, FIGS. 6 and 7 show the installation of a second set 58 of three fiducial markers 28 comprising a right fiducial marker 28d, a left fiducial marker 28e, and a front fiducial marker 28f. Arrows 60, 62 and 64 respectively represent attaching left fiducial marker 28d to a right portion 66 of second jaw 12b, attaching left fiducial marker 28e to a left portion 68 of second jaw 12b, and attaching front fiducial marker 28f to a front portion 70 of second jaw 12b. FIG. 6 shows markers 28d, 28e and 28f in their installed positions.

In some examples, the second set 58 of fiducial markers 28 provides a more precise indication of the second jaw's location and orientation than what is otherwise achieved by relying instead on distinct features 42 of teeth 44. This is because markers 28d, 28e, and 28f can be more spread out than teeth 44, and the size of marker bodies 36 is usually smaller than teeth 44.

Figure 8:
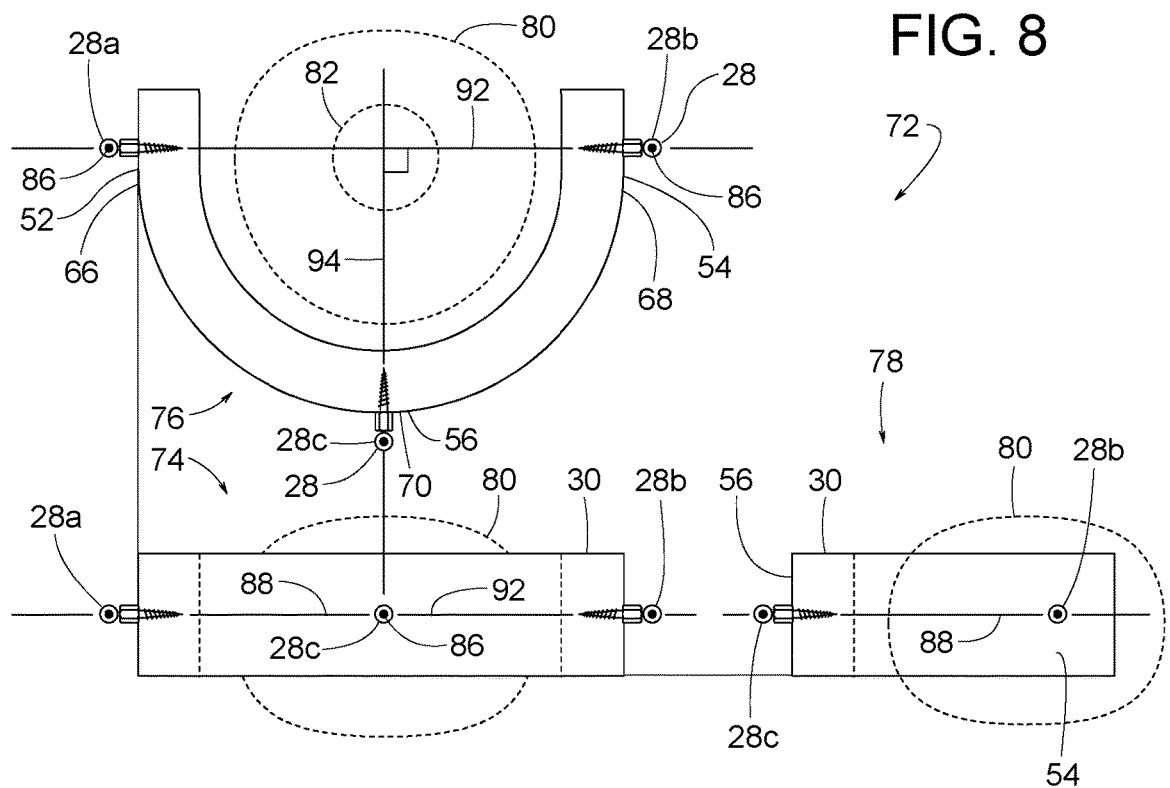
FIG. 8 is a set of orthogonal views showing an example scanning arrangement of fiducial markers screwed into in a schematically illustrated alveolar bone of either an upper or lower jaw.
Figure 9:
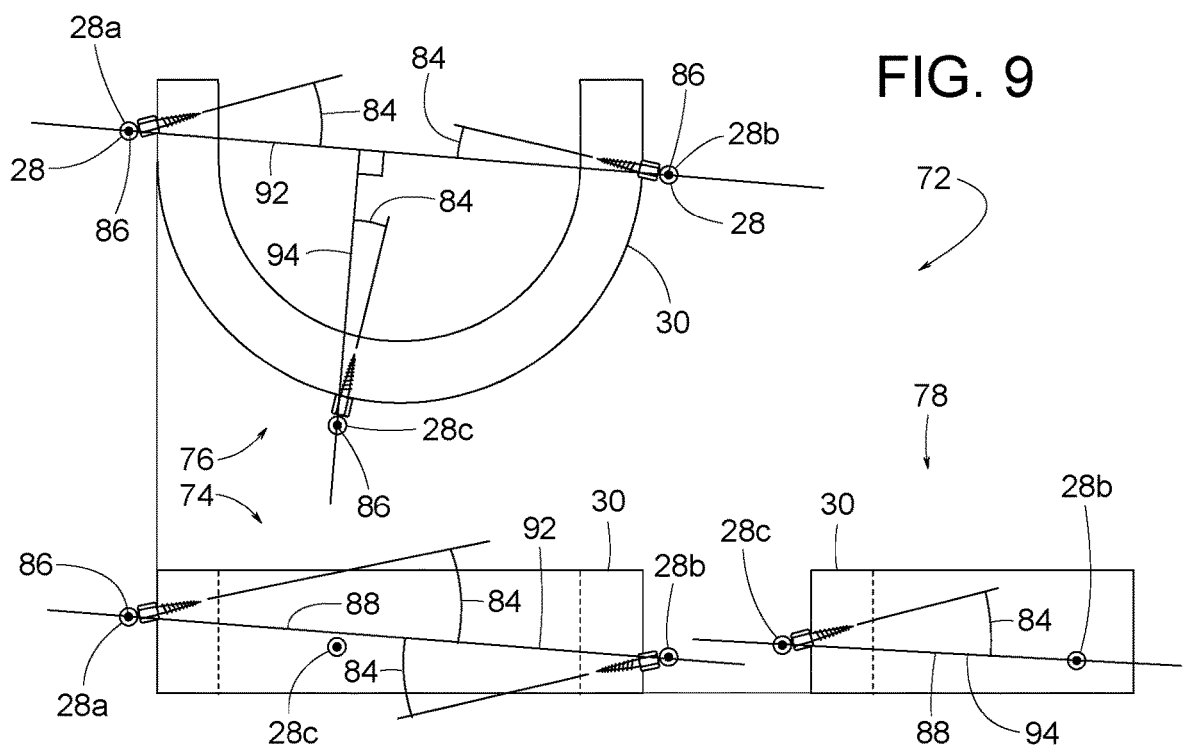
FIG. 9 is a set of orthogonal views showing another example scanning arrangement of fiducial markers screwed into in a schematically illustrated alveolar bone of either an upper or lower jaw.

FIGS. 8 and 9 are sets of orthogonal views showing example scanning arrangements 72 of fiducial markers 28 screwed into in a schematically illustrated alveolar bone 30 of either jaw member 12. FIG. 8 shows a front view 74, a top view 76, and a right side view 78 of jaw member 12 with fiducial markers 28 in an ideal arrangement. FIG. 9 shows the same views 74, 76 and 78 but with fiducial markers 28 in a more misaligned yet still acceptable configuration. From a vertical perspective, as shown in top view 76 of FIGS. 8 and 9, fiducial markers 28 extend beyond the general outer perimeter of jaw member 12 (i.e., outer perimeter in the vicinity of markers 28). Fiducial markers 28 thus provide a broader footprint for greater positional accuracy, as mentioned earlier.

FIGS. 8 and 9 show fiducial markers 28 and alveolar bone 30 in relation to an oral cavity 80 of patient 10. Oral cavity 80 is the area surrounded by alveolar bone 30. In the illustrated examples, screw 38 of each of the three fiducial markers 28 points inward toward a central region 82 of oral cavity 80 when fiducial markers 28 are attached to alveolar bone 30.

In some examples, for maxilla 12a, fiducial marker 28c is installed just below the midline of the anterior nasal spine, at the end of the superior labial frenulum. In some examples, fiducial markers 28a and 28b are installed just anterior of the maxillary tuberosity, with marker 28a on the right side and marker 28b on the left side.

In some examples, for mandible 12b, fiducial marker 28f is installed in the medial border of the hemi-mandible, near the alveolar crest. In some examples, fiducial markers 28d and 28e are installed along the oblique line, just below the posterior-most teeth, with marker 28d on the right side and marker 28e on the left side.

It has been discovered that the arrangements shown in FIGS. 8 and 9 provide good results when each fiducial marker's angular deviation (angle 84) is within 45 degrees of a predetermined ideal layout. More specifically, in the illustrated examples, each marker body 28 defines a center point 86 and are arranged such that:

a) center points 86 of fiducial markers 28a, 28b and 28c define a plane 88 (in some examples, plane 88 is generally parallel to an occlusal plane 90 of patient 10);

b) center point 86 of left fiducial marker 28b and center point 86 of right fiducial marker 28a define a lateral line 92 intersecting center point 86 of left fiducial marker 28b and center point 86 of right fiducial marker 28a;

c) center point 86 of front fiducial marker 28c defines a forward line 94 intersecting center point 86 of front fiducial marker 28c, intersecting lateral line 92, and being perpendicular to lateral line 92;

d) shaft 32 of left fiducial marker 28b lies within an angle 84 of 45 degrees of lateral line 92 as viewed from a direction perpendicular to plane 88;

e) shaft 32 of left fiducial marker 28b lies within an angle 84 of 45 degrees of lateral line 92 as viewed from a direction parallel to plane 88 and perpendicular to lateral line 92;

f) shaft 32 of right fiducial marker 28a lies within an angle 84 of 45 degrees of lateral line 92;

g) shaft 32 of right fiducial marker 28a lies within an angle 84 of 45 degrees of lateral line 92 as viewed from a direction parallel to plane 88 and perpendicular to lateral line 92;

h) shaft 32 of front fiducial marker 28c lies within an angle 84 of 45 degrees of forward line 94; and i) shaft 32 of front fiducial marker 28c lies within an angle 84 of 45 degrees of lateral line 92 as viewed from a direction parallel to plane 88 and perpendicular to lateral line 92.

Figure 10:
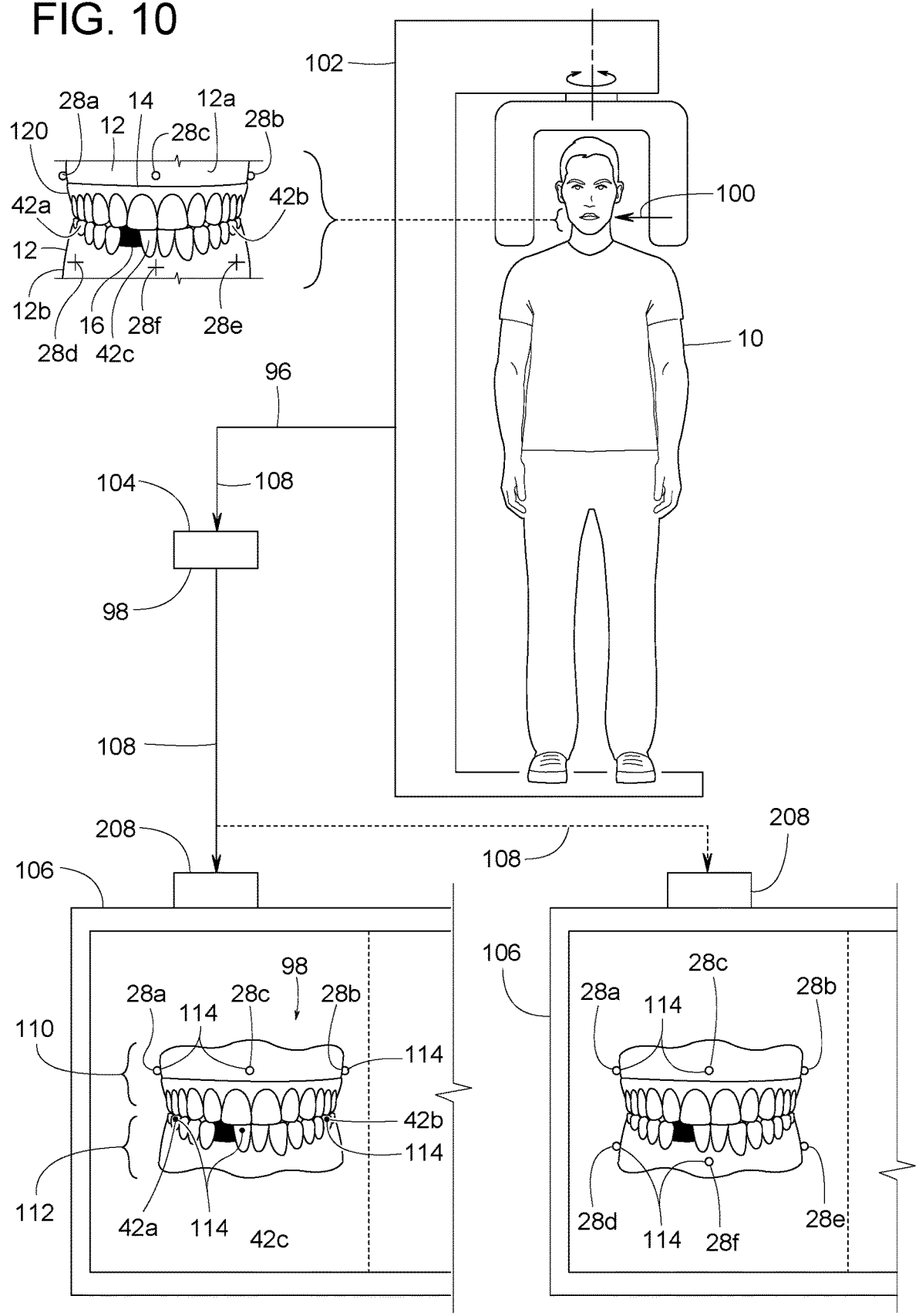
FIG. 10 is a schematic diagram illustrating various method steps associated with a first scanning machine.

In the example shown in FIGS. 4, 5 and 10, three fiducial markers 28a, 28b and 28c in upper jaw 12a and three features 42a, 42b and 42c of lower jaw 12b will be used as clear, distinct reference points for marking the location of upper jaw 12a relative to lower jaw 12b. Further steps in some examples of the present dental scanning method will now be explained with reference to FIGS. 10-24.

FIG. 10 illustrates creating 96 a first scan result 98 by scanning 100 first jaw 12a, second jaw 12b; three fiducial markers 28a, 28b and 28c on first jaw 12a; and three features 42a, 42b and 42c on second jaw 12b. In some examples, first scan result 98 is created by scanning 100 fiducial markers 28d, 28e and 28f in addition or alternatively to capturing features 42a, 42b and 42c.

In either case, scanning 100 is done while jaws 12 are in a predetermined target bite position relative to each other. In some examples, the predetermined target bite position is referred to as a proper bite registration, wherein the teeth and/or other installed dental appliances fit comfortably together in a generally closed position without subjecting the temporamandibular joints to undo stress. An example of such a predetermined target bite position, or proper bite registration, is shown in FIG. 2 and the upper left corner of FIG. 10.

The term, "dental appliance" refers to any device temporarily or permanently installed within a patient's mouth. Some example dental appliances include full dentures, partial dentures, bridges, crowns, cavity fillings, braces, implants, etc. In some examples, dental appliances and a patient's actual teeth are some examples of "spacers," as both teeth and dental appliances limit how closely upper jaw 12a and lower jaw 12b can come together.

Scanning 100, as shown in FIG. 10, can be done by any suitable scanning method. Some example methods of scanning 100 include cone beam computed tomography (CBCT), magnetic resonance imaging (MRI), computed tomography (CT or CAT), X-ray, etc. In some examples, scanning 100 is performed using a CBCT scanning machine 102 (first scanning machine 102). Some examples of first scanning machine 102 include an i-Cat FLX.I cone beam 3D imaging scanner manufactured by Imaging Sciences International LLC of Alpharetta, Ga. or Hatfield, Pa.

From first scanning machine 102, first scan result 98 is transferred in a file format 104 to a computer 106, as indicated by arrows 108 of FIG. 10. In some examples, first scanning machine 102 generates first scan result 98 in a first format (e.g., a dicom file), and computer 106 converts the first format to a more manageable digital format (e.g., an stl file). In some examples, the file conversion is accomplished through dental treatment planning software executed by computer 106. Some examples of such software include exocad, 3shape, dental wings, and Dentsply Sirona. In other examples, first scanning machine 102 generates first scan result 98 directly in a more manageable digital format without the need for subsequent file conversion by computer 106.

FIG. 10 also shows computer 106 displaying first scan result 98 including a first scanned representation of the first jaw 110, a first scanned representation of the second jaw 112, and a first constellation of points 114. In some examples, first constellation of points 114 represents three fiducial markers 28a, 28b and 28c; as shown in the left-bottom of FIG. 10. In some examples, first constellation of points 114 represents three fiducial markers 28a, 28b and 28c on first jaw 12a plus three features 42a, 42b and 42c on second jaw 12b; also shown in the left-bottom of FIG. 10. In some examples, first constellation of points 114 represents three fiducial markers 28a, 28b and 28c on first jaw 12a plus second set 58 of three fiducial markers 28d, 28e and 28f on second jaw 12b; shown in the right-bottom of FIG. 10.

First scan result 98, regardless of which example of first constellation of points 114 is being used, provides a reference against which subsequent scans will be compared. Such later scans will be used for creating an accurate digital jaw model 116 (FIGS. 20, 23 and 24) that can be manipulated and analyzed in the treatment of patient 10. Various method steps for producing such scans are shown in FIGS. 11-14.

Figure 14:
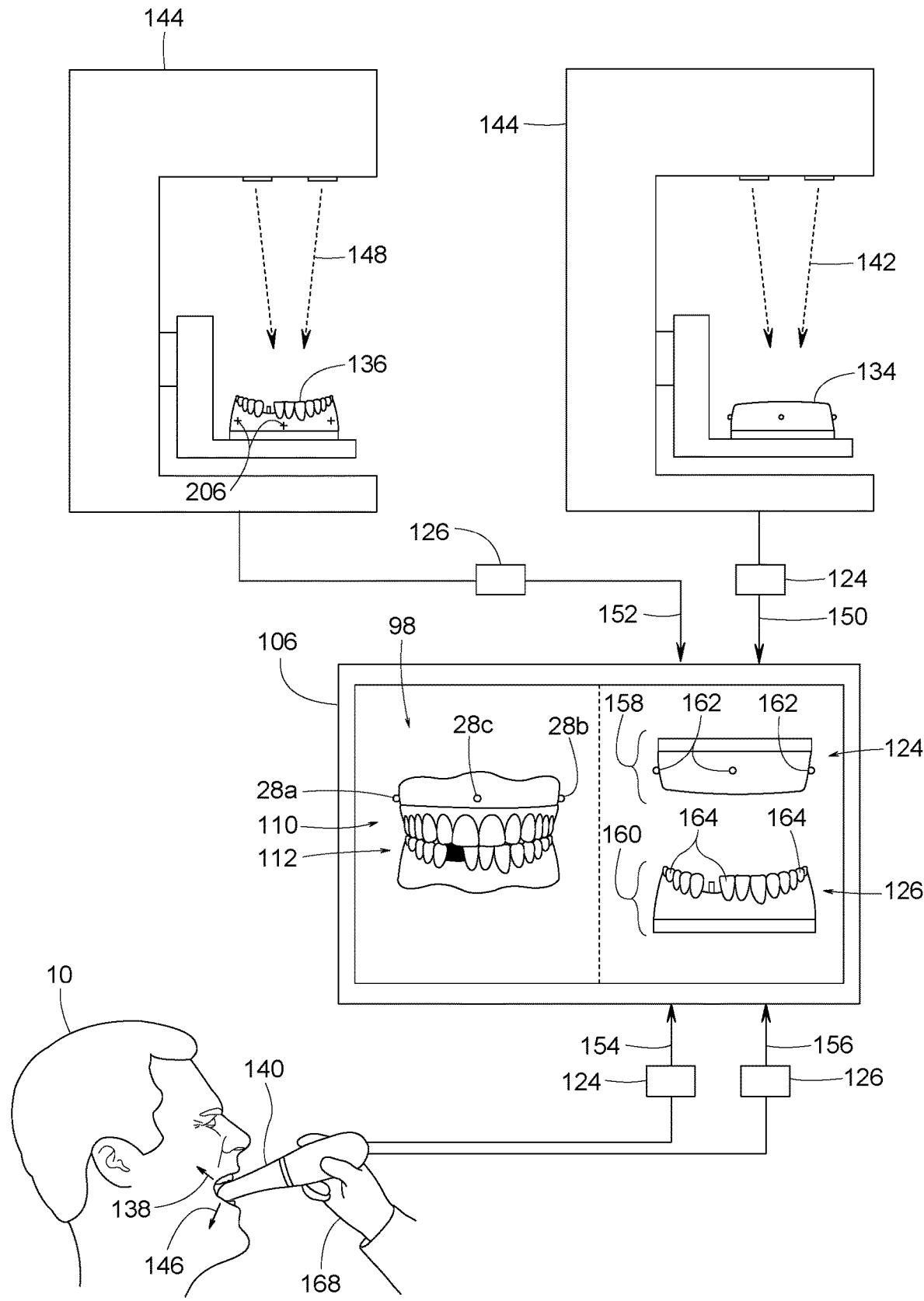
FIG. 14 is a schematic diagram showing additional example scanning methods.

Arrow 118 of FIG. 11 represents old dentures 14 being removed from the patient's upper jaw 12a. Since dentures 14 limit how closely jaws 12 can close, dentures 14 are considered as being a spacer 120, and arrow 118 represents removing spacer 120 from patient 10. In this example, arrows 122 represent attaching implant 20 (e.g., anchor 22 and post 26) to lower jaw 12b, thus arrows 122 more broadly represent attaching implant 20 to at least one of first jaw 12a and second jaw 12b and doing so after creating first scan result 98 (FIG. 10) but before creating at least one of a second scan result 124 (FIG. 14) and a third scan result 126 (FIG. 14). FIG. 10, on the other hand, shows jaws 12 being scanned while spacer 120 (e.g., old dentures 14) are still in place to help position jaws 12 at the predetermined target bite position for proper bite registration.

FIG. 12 illustrates a conventional method of using a known molding material 128 for creating molds 130 and 132 of jaws 12a and 12b, respectively. In this example, molds 130 and 132 capture the contours of jaws 12a and 12b including the shapes of implant 20; markers 28a, 28b and 28c; features 42a, 42b and 42c; the void due to the omission of dentures 14; and markers 28d, 28e and 28f (if used). Molds 130 and 132, however, can be independent of each other, so they do not necessarily capture the relative positions of jaws 12a and 12b.

Molds 130 and 132 produce a physical model 134 of first jaw 12a and a physical model 136 of second jaw 12b, as shown in FIG. 13. In some examples, models 134 and 136 are castings created within the mold cavities of molds 130 and 132. Such methods of creating physical models 134 and 136 are well known to provide accurate reproductions of the surface geometries of jaws 12.

FIG. 14 illustrates creating second scan result 124 by scanning 138 first jaw 12a directly via a scanner 140 or scanning 142 the physical model 134 of first jaw 12a via a scanner 144. FIG. 14 also illustrates creating third scan result 126 by scanning 146 second jaw 12b directly via scanner 140 or scanning 148 the physical model 136 of second jaw 12b via scanner 144. Some examples of scanner 140 include a Carestream CS3600 intraoral scanner provided by Carestream Dental LLC of Rochester, N.Y. or Atlanta, Ga. Some examples of scanner 144 include a Medit Identica T500 benchtop scanner of Seoul, South Korea.

In some examples, using scanner 144 for scanning models 134 and 136 provides a sharper, more distinct image of individual jaws 12a and 12b than what can be achieved with scanner 102 (FIG. 10). Scanner 102, however, provides a clear representation of the jaws' relative position in their natural bite registration. So, there is a benefit to using both scanners 102 and 144, wherein scanner 102 is an example of a first scanning machine, scanner 144 is an example of a second scanning machine, and scanners 102 and 144 are two different scanning machines.

Using intraoral scanner 140 for scanning jaws 12 directly is an alternative to using scanner 144. Scanner 140 eliminates the need for creating models 134 and 136; however, scanner 140 might accumulate a series of incremental positional errors while traversing a significant distance across jaws 12. Both scanners 140 and 144 are considered "second scanning machines" and each one is different than first scanning machine 102.

Regardless of which second scanning machine 140 or 144 is used, scanners 140 and 144 generate second scan result 124 representing upper jaw 12a and third scan result 126 representing lower jaw 12b. Arrow 150 represents transmitting second scan result 124 of upper jaw model 134 from scanner 144 to computer 106, arrow 152 represents transmitting third scan result 126 of lower jaw model 136 from scanner 144 to computer 106, arrow 154 represents transmitting second scan result 124 of upper jaw 12a to computer 106, and arrow 156 represents transmitting third scan result 126 of lower jaw 12b to computer 106.

In response to receiving scan information from scanner 140 or 144, computer 106 displays second scan result 124 and third scan result 126, as shown in FIG. 14. Second scan result 124 includes a second scanned representation of the first jaw 158 and a second constellation of points 162 representing the three fiducial markers 28a, 28b and 28c. Third scan result 126 includes a second scanned representation of the second jaw 160. In some examples, third scan result 126 further includes a third constellation of points 164 representing features 42a, 42b and 42c and/or representing the second set of fiducial markers 28d, 28e and 28f.

In some examples, the first constellation of points 114, the second constellation of points 162, and/or the third constellation of points 164 are used as reference points in shifting the individual jaw images in the second scan to match the properly fitting jaw image in the first scan. In other words, shifting second scanned representation of the first jaw 158 (e.g., upper jaw 12a) relative to second scanned representation of the second jaw 160 (e.g., lower jaw 12b) so they align with first scanned representation of the first jaw 119 (e.g., upper jaw 12a) and first scanned representation of the second jaw 112 (e.g., lower jaw 12b). The goal is to shift the sharp, clear individual jaw images of jaws 12a and 12b in the second scan (FIG. 14) according to the bite registration of the first scan (FIG. 10) to create the precise digital jaw model 116 (FIGS. 20, 23 and 24) that can be manipulated and analyzed to aid in various orthodontic and other dental treatments.

FIGS. 15-20 illustrate an example of creating digital jaw model 116 (FIG. 20) by shifting (arrows 166 of FIG. 19) the second scanned representation of the first jaw 158 relative to second scanned representation of the second jaw 160 such that the second constellation of points 162 relative to the second scanned representation of the second jaw 160 substantially coincides with the first constellation of points 114 relative to the first scanned representation of the second jaw 112.

In some examples, creating an association of fiducial markers 28 and/or features 42 in the second and third scan results 124 and 126 and the corresponding fiducial markers 28 and/or features 42 in the first scan result 98, involves a dental practitioner 168 (e.g., a dentist, a lab technician, etc.) manually identifying via mouse-clicking 170 on select pairs of points of constellations 114, 162 and 164 for which associations are to be established. Constellations 114, 162 and 164 each comprise a plurality of individual points 172. Mouse-clicking 170 is one example method for manually identifying where the plurality of individual points 172 are located in space (e.g., identifying their coordinates) and for determining how far at least some of the plurality of individual points 172 should be shifted.

Figure 21:
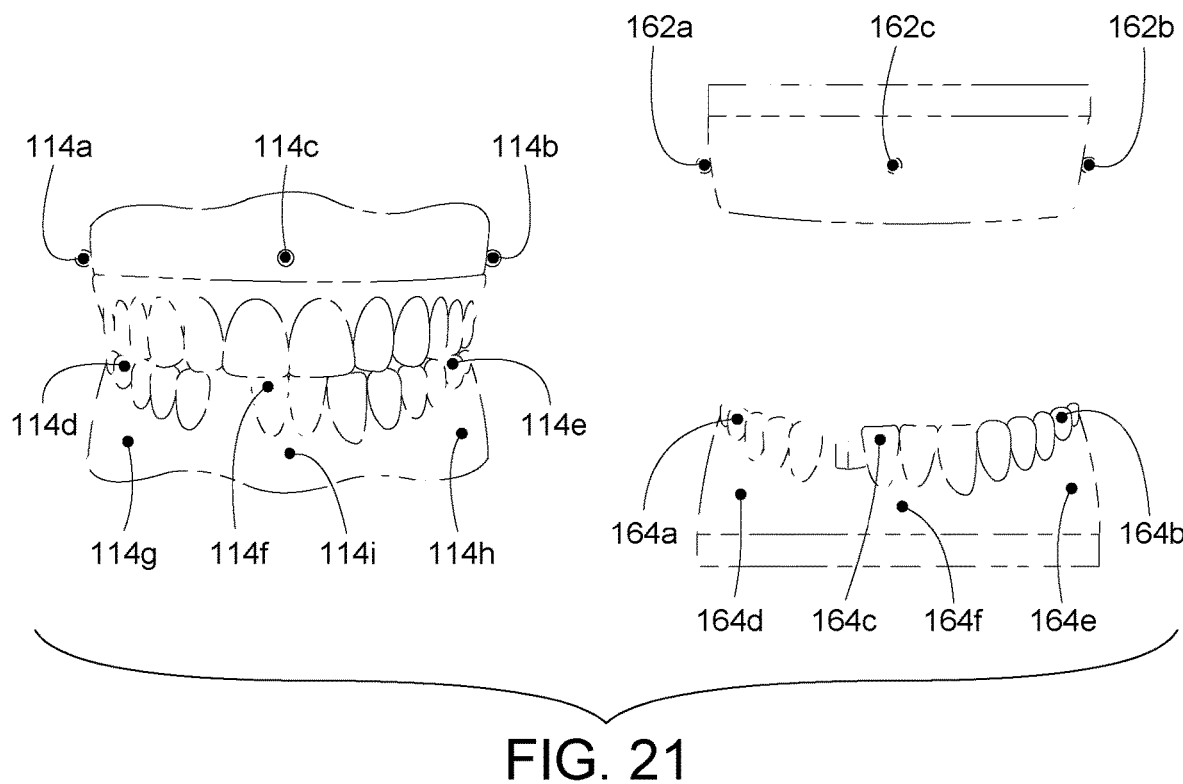
FIG. 21 is a front view of example jaw images that include some example constellations of points.

In some examples, referring to FIG. 21, first constellation of points 114 includes points 114a, 114b and 114c, which correspond to fiducial markers 28a, 28b and 28c, respectively. In addition or alternatively, some examples of first constellation of points 114 includes points 114d, 114e and 114f, which correspond to features 42a, 42b and 42c, respectively. In addition or alternatively, some examples of first constellation of points 114 includes points 114g, 114h and 114i, which correspond to fiducial markers 28d, 28e and 28f, respectively.

In some examples, second constellation of points 162 includes points 162a, 162b and 162c, which correspond to fiducial markers 28a, 28b and 28c, respectively.

In some examples of third constellation of points 164 includes points 164a, 164b and 164c, which correspond to features 42a, 42b and 42c, respectively. In addition or alternatively, some examples of third constellation of points 164 includes points 164d, 164e and 164f, which correspond to fiducial markers 28d, 28e and 28f, respectively.

In some examples, a composite constellation of points 174 comprises a combination of the second and third constellation of points 162 and 164. Some examples of the composite constellation of points 174 include points 162a, 162b and 162c plus points 164a, 164b and 164c. Some examples of the composite constellation of points 174 include points 162a, 162b and 162c plus points 164d, 164e and 164f.

Figure 15:
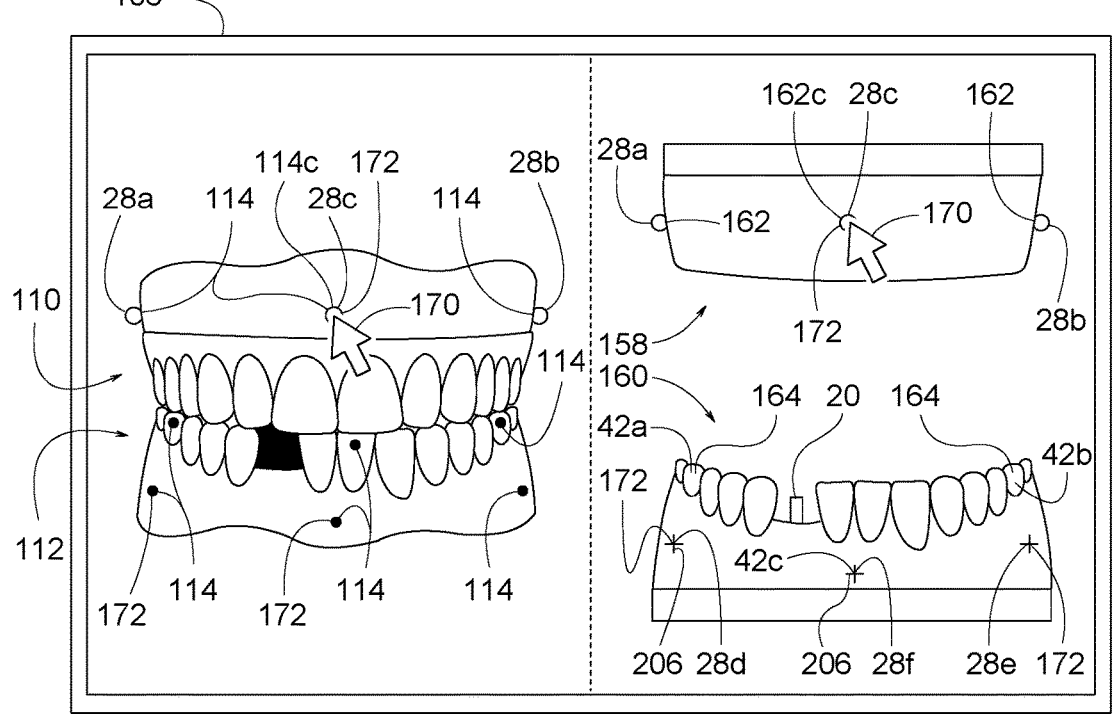
FIG. 15 is front view of a computer displaying multiple scan results of jaws and a schematic depiction of a dental practitioner mouse-clinking on certain points of the scan results.

FIG. 15 illustrates mouse-clicking 170 on point 114c of first constellation of points 114 and mouse-clicking 170 on point 162c of second constellation of points 162. In response to such mouse-clicking, computer 106 determines that points 114c and 162c represent the same point (marker 28c) on first jaw 12a.

Figure 16:
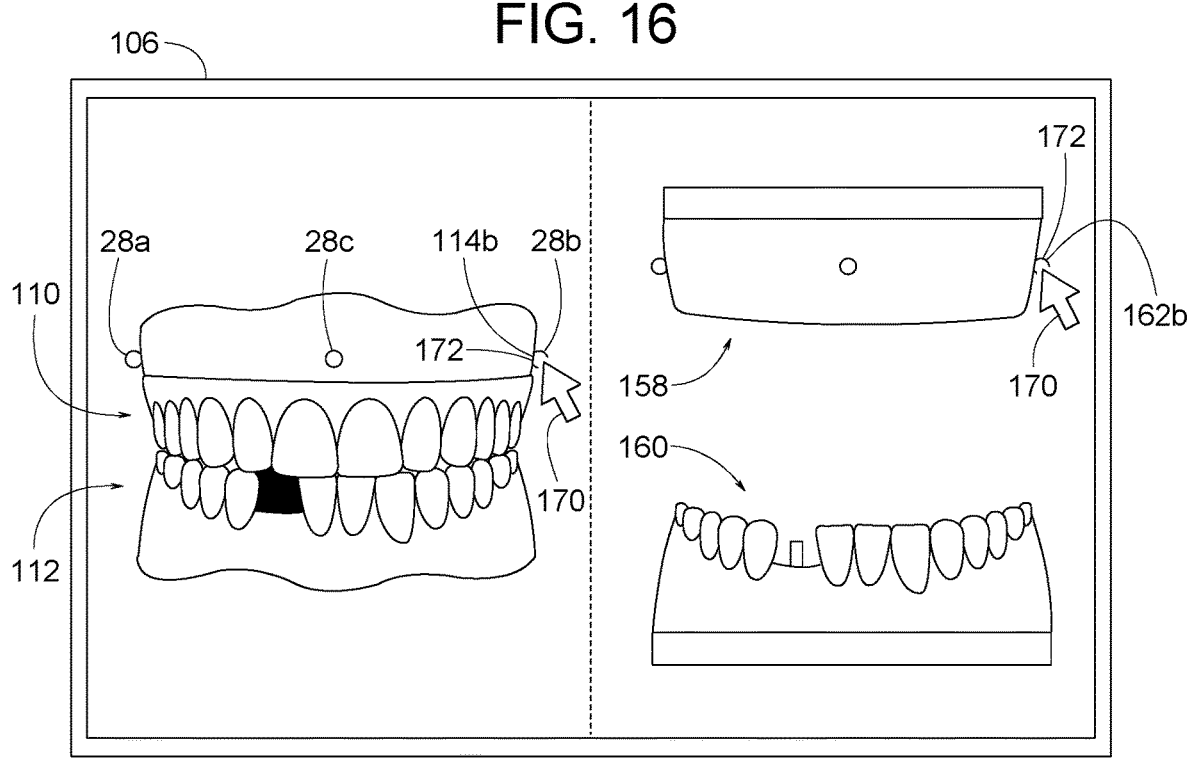
FIG. 16 is front view similar to FIG. 15 but showing a schematic depiction of the dental practitioner mouse-clinking on other points of the scan results.

FIG. 16 illustrates mouse-clicking 170 on point 114b of first constellation of points 114 and mouse-clicking 170 on point 162b of second constellation of points 162. In response to such mouse-clicking, computer 106 determines that points 114b and 162b represent the same point (marker 28b) on first jaw 12a.

Likewise, similar mouse-clicking on point 114a of first constellation of points 114 and mouse-clicking 170 on point 162a of second constellation of points 162 is interpreted as meaning that points 114a and 162a represent the same point (marker 28a) on first jaw 12a.

Figure 17:
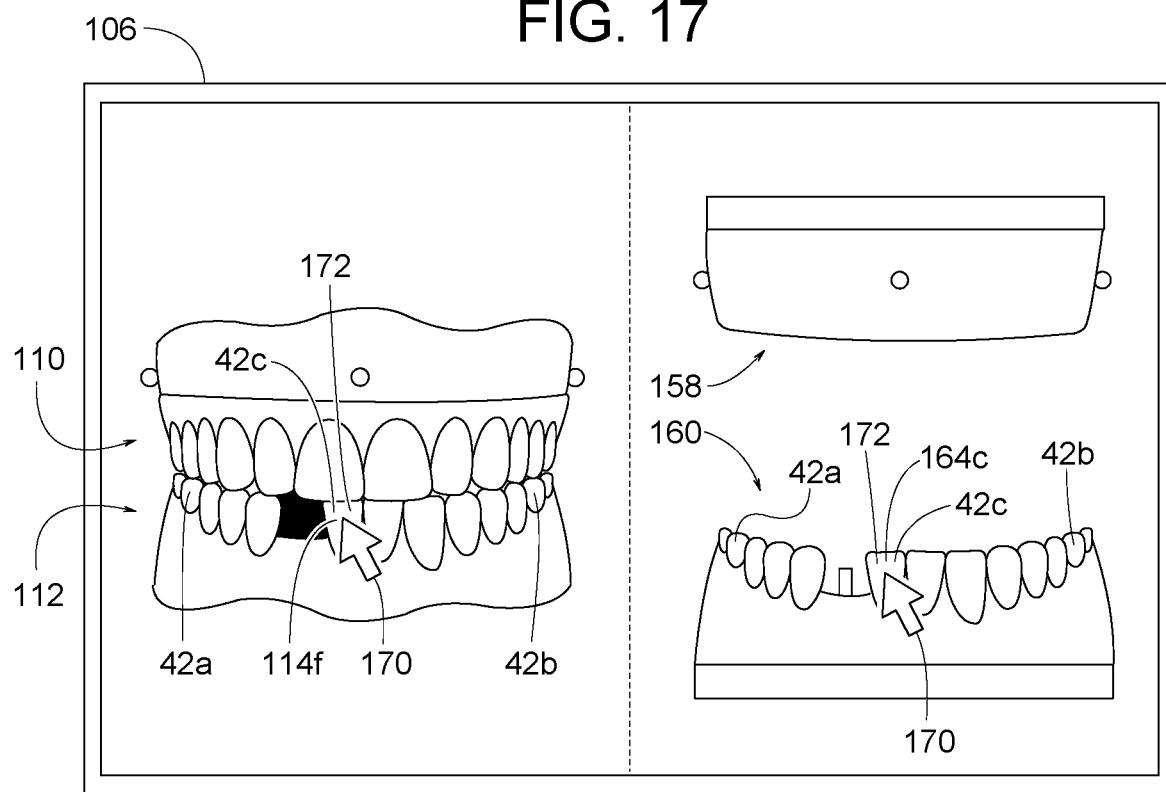
FIG. 17 is front view similar to FIG. 15 but showing a schematic depiction of the dental practitioner mouse-clinking on additional points of the scan results.
Figure 18:
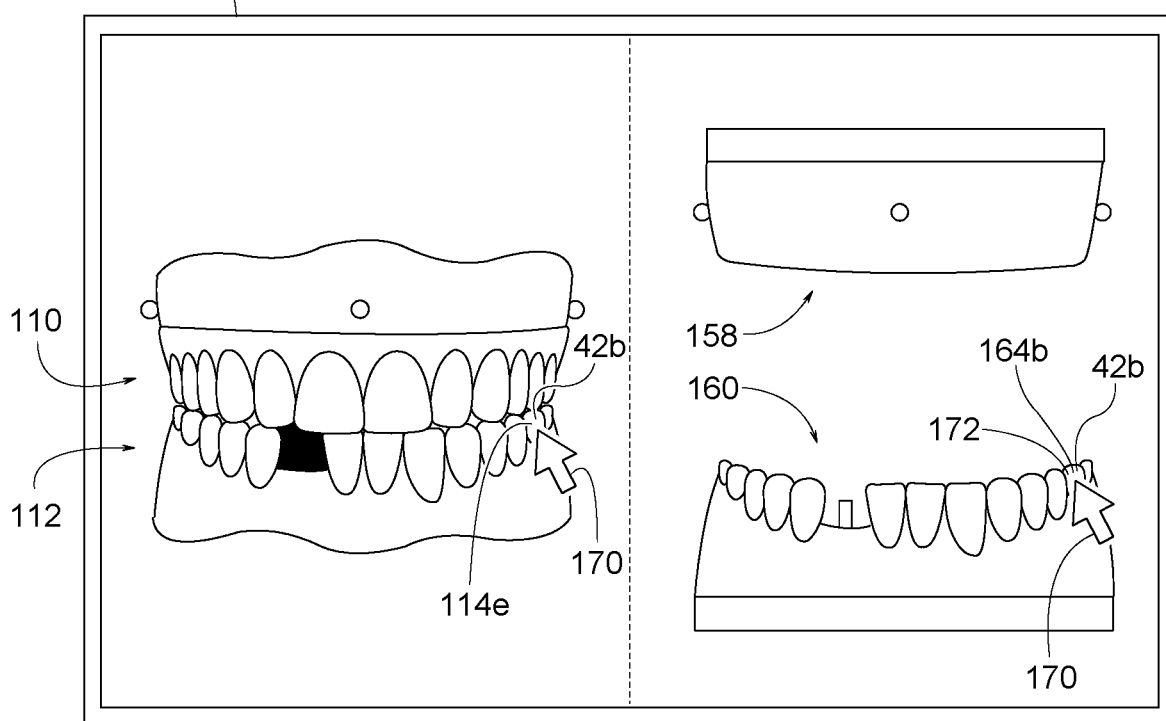
FIG. 18 is a front view similar to FIG. 15 but showing a schematic depiction of the dental practitioner mouse-clinking on even more points of the scan results.

FIGS. 17 and 18 show a similar process being applied to second jaw 12b. FIG. 17 illustrates mouse-clicking 170 on point 114f of first constellation of points 114 and mouse-clicking 170 on point 164c of third constellation of points 164. In response to such mouse-clicking, computer 106 determines that points 114f and 164c represent the same point (feature 42c) on second jaw 12b.

FIG. 18 illustrates mouse-clicking 170 on point 114e of first constellation of points 114 and mouse-clicking 170 on point 164b of third constellation of points 164. In response to such mouse-clicking, computer 106 determines that points 114e and 164b represent the same point (feature 42b) on second jaw 12b. Likewise, similar mouse-clicking on point 114d of first constellation of points 114 and mouse-clicking 170 on point 164a of third constellation of points 164 is interpreted as meaning that points 114d and 164a represent the same point (feature 42a) on second jaw 12b.

The mouse-clicking method, as just described with reference to FIGS. 15-18, ties the second scan representation of the first jaw 158 (e.g., upper jaw 12a) to the first scan representation of the first jaw 110 (e.g., upper jaw 12a). Such mouse-clicking also ties the second scan representation of the second jaw 160 (e.g., lower jaw 12b) to the first scan representation of the second jaw 112 (e.g., lower jaw 12b).

Figure 19:
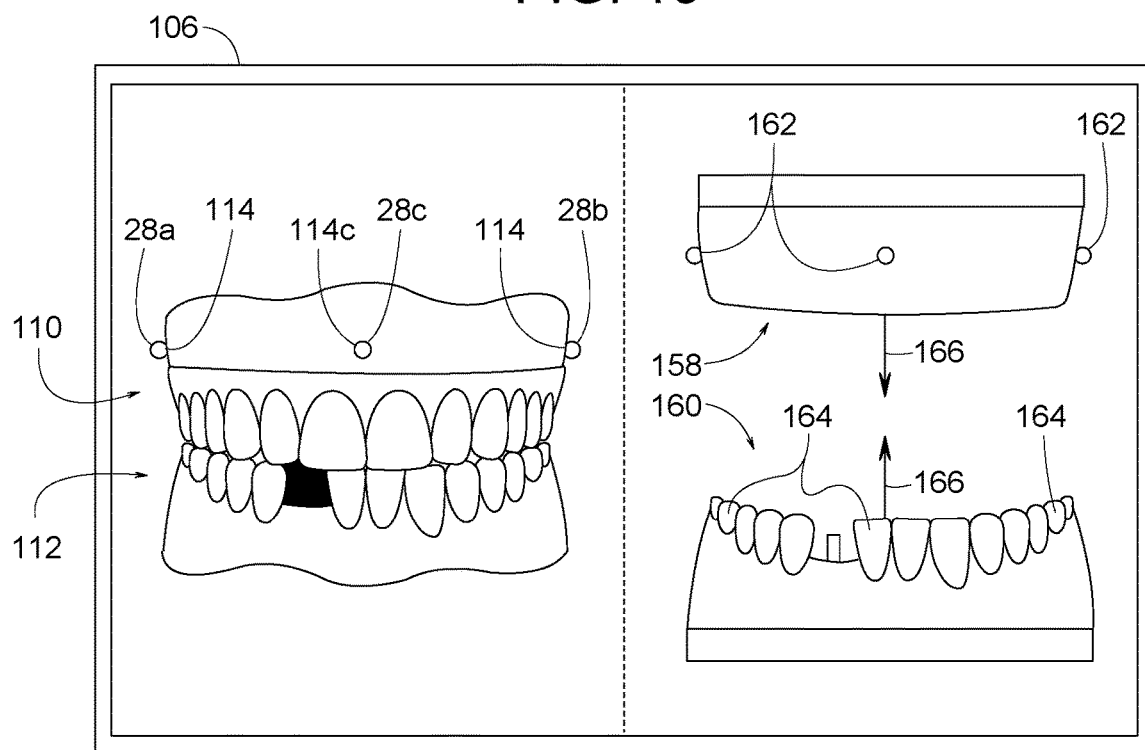
FIG. 19 is a front view similar to FIGS. 15-18 showing upper and lower jaws on the right side of the computer display being shifted to create a digital jaw model having a bite registration that matches that of the upper and lower jaws on the left side.
Figure 20:
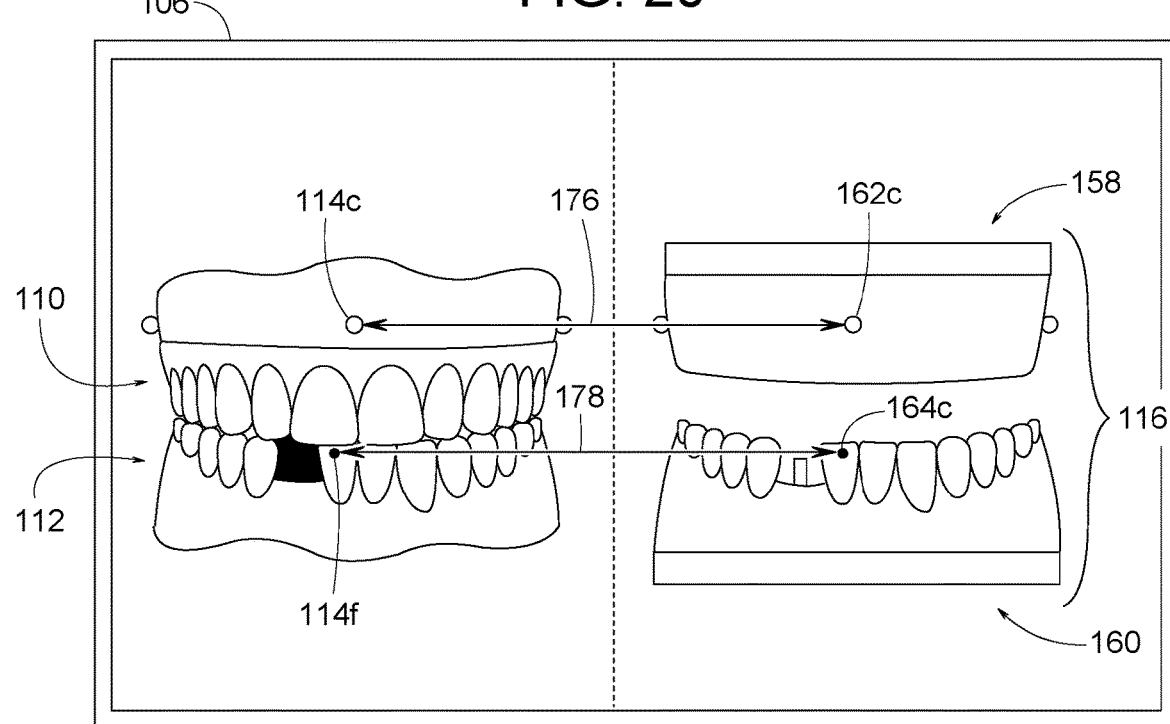
FIG. 20 is a front view similar to FIG. 19 but showing the upper and lower jaws on the right side having been shifted so as to coincide with the positional relationship of the upper and lower jaws on the left side, whereby the jaws on both sides of the display have substantially the same bite registration.

Next, as shown in FIG. 19, arrows 166 represent shifting the second constellation of points 162 and the third constellation of points 164 relative to each other such that both the second constellation of points 162 and the third constellation of points 164 of the composite constellation of points 174 substantially coincide with the first constellation of points 114. Such shifting creates digital jaw model 116, as shown in FIG. 20, arrow 176 shows how well point 162c of second constellation of points 162 aligns with point 114c of first constellation of points 114. Arrow 178 shows how well point 164c of third constellation of points 164 aligns with point 114f of first constellation of points 114. Consequently, second scan representation of the first jaw 158 and second scan representation of the second jaw 160, of digital jaw model 116, are positioned in proper bite registration in accordance with the bite registration recorded in first scan result 98.

Figure 23:
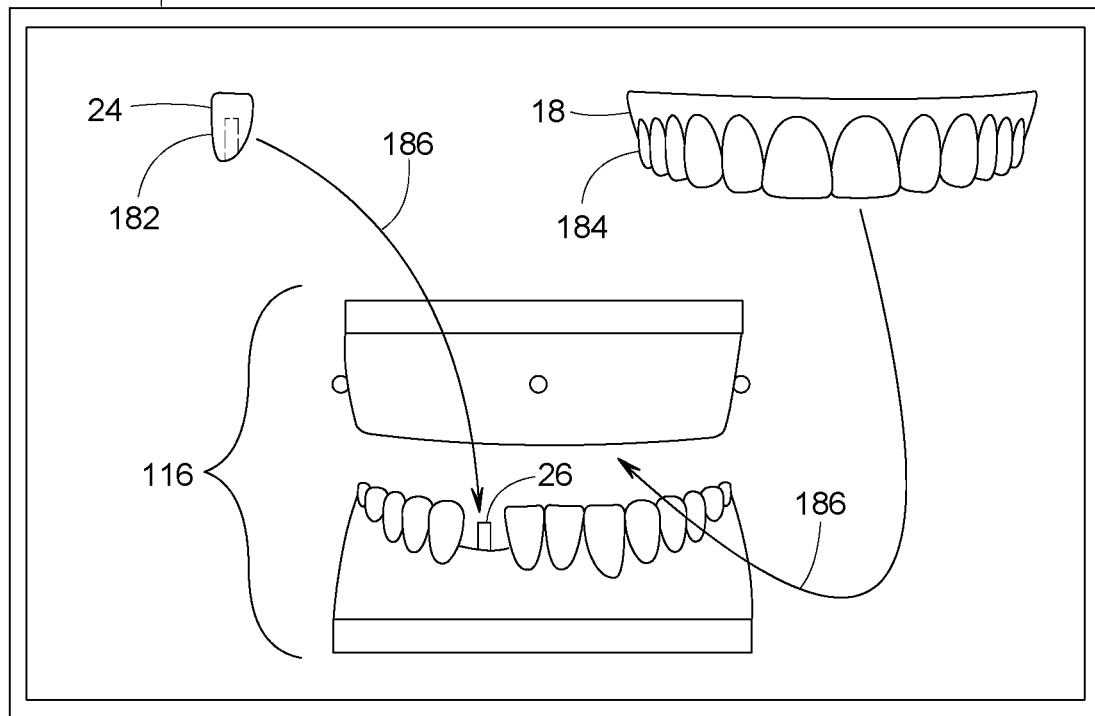
FIG. 23 is a front view of the computer displaying the recently created digital jaw model with virtual teeth and virtual dentures being fitted to the digital jaw model.
Figure 24:
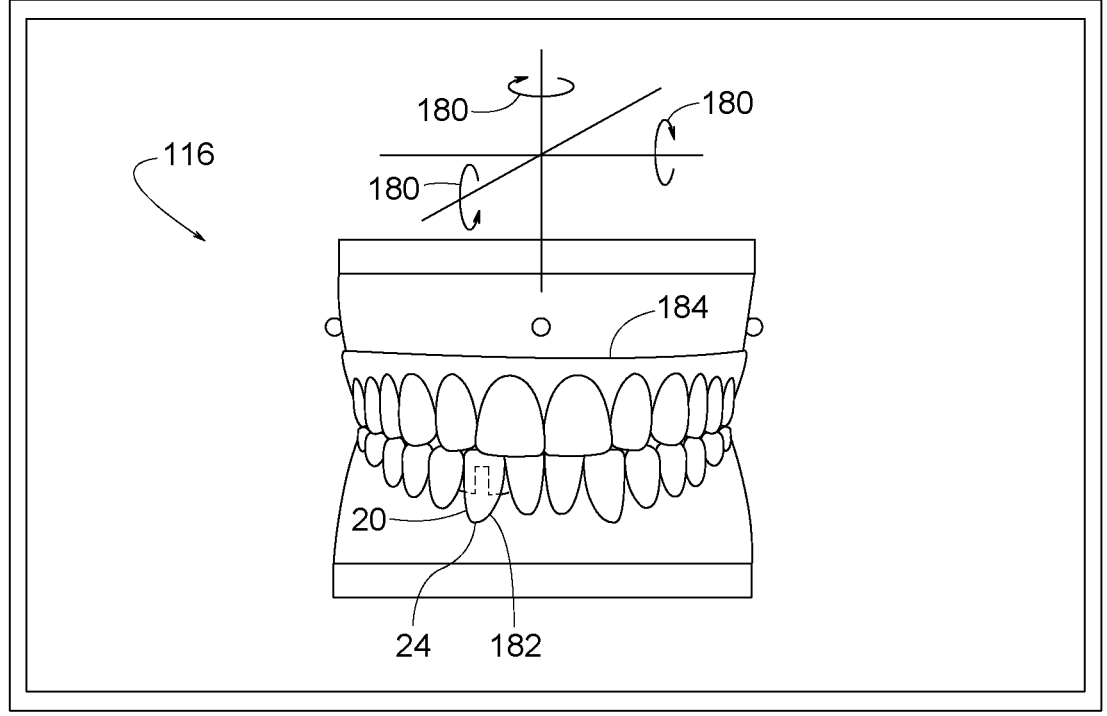
FIG. 24 is a front view similar to FIG. 23 but with the virtual dental appliances fitted in position.

Once digital jaw model 116 is configured in its proper bite registration, first scan result 98 can be set aside, and dental practitioner 168 can now focus on digital jaw model 116, as shown in FIGS. 23 and 24). To help analyze jaws 12 in the treatment of patient 10, dental practitioner 168 can view digital jaw model 116 from different angles, as known software (e.g., exocad, 3shape, dental wings, Dentsply Sirona, etc.) enables computer 106 to rotate digital jaw model 116 in virtual 3D space. Such 3D rotation is represented by arrows 180 in FIG. 24.

Figure 22:
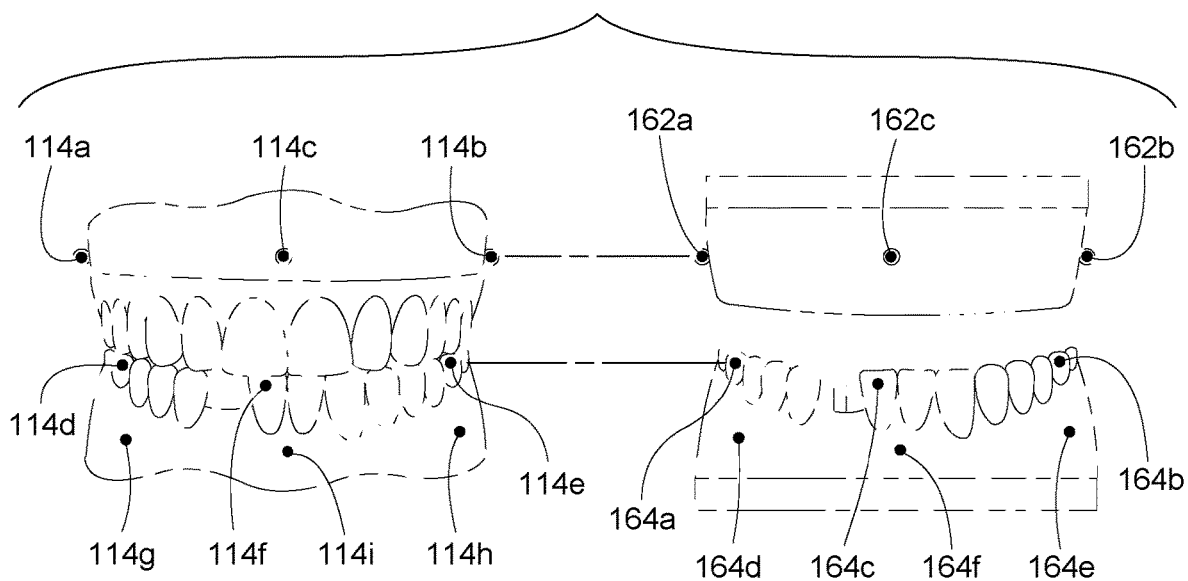
FIG. 22 is a front view similar to FIG. 21 but with some of the constellations of points shifted to another position.

In the example illustrated in FIGS. 21 and 22, dental practitioner 168 fits a virtual crown 182 (crown 24) and a virtual new set of dentures 184 (dentures 18) to digital jaw model 116. Arrows 186 of FIG. 23 represents adding a virtual dental appliance (e.g., crown 24, dentures 18, etc.) to digital jaw model 116. FIG. 24 shows the expected appearance and fit of crown 24 and dentures 18. If the appearance and fit are acceptable, dental practitioner 168 can 3D print, machine or otherwise create an actual physical crown 24 and dentures 18 that match the proposed virtual ones.

Although fiducial markers 28 can be of any suitable shape and design, FIGS. 25-27 show three examples. In FIG. 25, marker body 36 is generally spherical and is overmolded directly onto an integral extension 188 of screw 38. The slenderness of extension 188 minimizes radiographic interference with marker body 36.

In FIG. 26, marker body 36 is overmolded onto a pin 190 that is sized to fit within a blind hole 192 in screw 38. This allows marker body 36 to be attached to screw 38 for scanning and molding purposes and otherwise removed for the comfort of patient 10. In some examples, pin 190 has a shoulder 194 that ensures repeatable positioning of marker body 36 relative to screw 38. In some examples, pin 190 is tapered for tightly securing pin 190 to screw 38 and for establishing a repeatable stop position of pin 190 within a similarly tapered version of hole 192. Arrows 196 represent selectively attaching marker body 36 to screw 38 and separating marker body 36 from screw 38.

In FIG. 27, a spherical dimple 198 in head 40 of screw 38 provides a suitable surface to which a glue 200 can adhesively bond marker body 36 to head 40. A breakable adhesive bond provides a means for selectively attaching 202 marker body 36 to screw 38 and separating 204 marker body 36 from screw 38.

Here are some additional points worth noting. In FIGS. 14 and 15, marks 206 schematically represent the optional second set 58 of three fiducial markers 28d, 28e and 28f Thus, arrows 146 and 148 of FIG. 14 also represents creating third scan result 126 by not only scanning at least one of the second jaw 12b and physical model 136 of second jaw 12b but by also scanning at least one of second set 58 of three fiducial markers 28d, 28e and 28f attached to second jaw 12b and physical model 136 with an indication (visual image) of the three fiducial markers 28d, 28e and 28f thereon.

In FIG. 10, blocks 208 represent converting first scan result 98 to a digital format substantially equal in format to that of second scan result 124 and third scan result 126. In some examples, the file converting step of block 208 is accomplished through dental treatment planning software executed by computer 106. As mentioned earlier, some examples of such software include exocad, 3shape, dental wings, and Dentsply Sirona. Some example file types include various versions of open mesh data, point cloud data, and DentalCAD HTML scenes. Some specific example file format extensions include .stl, .obj, .ply, .off, .eoff, .xyz, .xyznb.

Arrow 96 of FIG. 10 illustrates creating first scan result 98 by concurrently scanning 100 first jaw 12a and second jaw 12b of patient 10. FIG. 14 illustrates creating second scan result 124 by scanning (arrows 138 and 142) at least one of first jaw 12a and physical model 134 of first jaw 12a, wherein creating first scan result 98 is accomplished using first scanning machine 102, creating second scan result 124 is accomplished using second scanning machine 144, and first scanning machine 102 and second scanning machine 144 are two different machines. FIG. 14 also illustrates creating third scan result 126 by scanning (arrows 146 and 148) at least one of second jaw 12b and physical model 136 of second jaw 12b.

Computer 106 in FIG. 14 illustrates displaying first scan result 98 including first scanned representation of the first jaw 110 (upper jaw 12a) and first scanned representation of the second jaw 112 (lower jaw 12b) in a first positional relationship relative to each other (e.g., jaws 12 in a predetermined proper bite registration). Computer 106 in FIG. 14 illustrates displaying second scan result 124 including second scanned representation of the first jaw 158. Computer 106 in FIG. 14 illustrates displaying third scan result 126 including second scanned representation of the second jaw 160 in a second positional relationship (e.g., jaws 12a and 12b widely spaced apart) relative to second scanned representation of the first jaw 158.

Arrows 166 of FIG. 19 illustrates shifting second scanned representation of the first jaw 158 relative to second scanned representation of the second jaw 160 such that the second positional relationship of second scanned representation of the first jaw 158 relative to the second scanned representation of the second jaw 160 is substantially equal to (as indicated by arrows 176 and 178 of FIG. 20) the first positional relationship of the first scanned representation of the first jaw 110 relative to the first scanned representation of the second jaw 112.

Arrow 118 of FIG. 11 illustrates removing at least one of a tooth and a dental appliance (e.g., dentures 14) from patient 10 after creating first scan result 98 but before creating second scan result 124. Otherwise, failing to remove such items would interfere with second scan result 124 and/or third scan result 126 and thus interfere with planning of the patient's treatment.

FIGS. 28-49 pertain to example radiographic dental jigs 220 (e.g., radiographic dental jigs 220a-220d) and example methods of using them. Jigs 220 can be used in dental radiography to help record a patient's actual or desired incisal edge plane 222 and/or a reference location of a patient's lips 224.

Although the actual design may vary, jigs 220 basically include a post 226 and a beam 228. Beam 228 traverses post 226 to create a cross 230. While post 226 may be considered to be generally vertical and beam 228 generally horizontal, cross 230, of course, can be positioned in any spatial orientation.

The term, "cross" refers to two adjoining elongate members (e.g., post 226 and beam 228) that lie substantially perpendicular to each other. The point at which the two elongate members cross can be at any location along the length of each elongate member. In some examples, for instance, the two elongate members intersect at a central point of each elongate member, thereby creating a shape that resembles a plus sign. In other examples, some point along one of the elongate members is at or near one end of the other elongate member, such that the cross resembles a T-shape, an inverted T-shape, an L-shape, etc.

In the illustrated examples, post 226 and beam 228 are substantially perpendicular and intersecting. In other examples, however, post 226 and beam 228 are perpendicular to each other but are nonintersecting. In other words, in some examples, post 226 and beam 228 are offset in a direction that is perpendicular to both post 226 and beam 228, e.g., post 226 is slightly in front of or behind beam 228.

Figure 28:
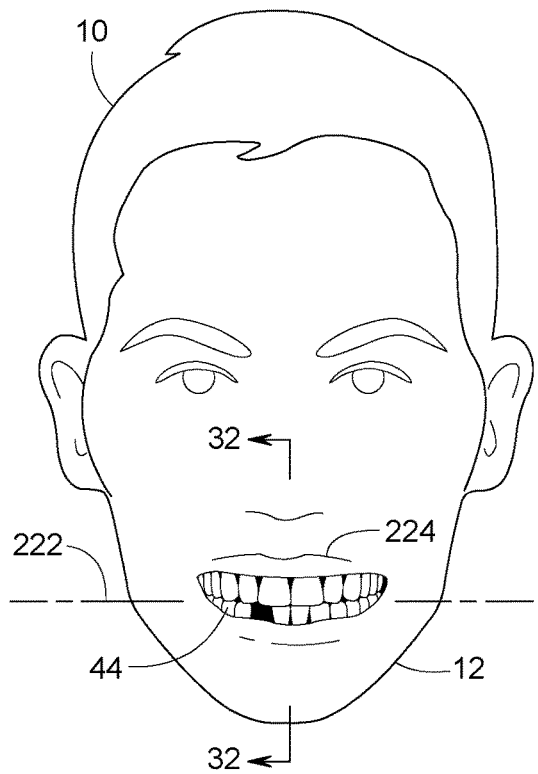
FIG. 28 is a front view of an example patient.

FIG. 28 is nearly the same as FIG. 2 and shows patient 10 in an upright position and prior to the installation of jig. 220. FIG. 28 shows the incisal edge plane 222 of patient 10.

Figure 29:
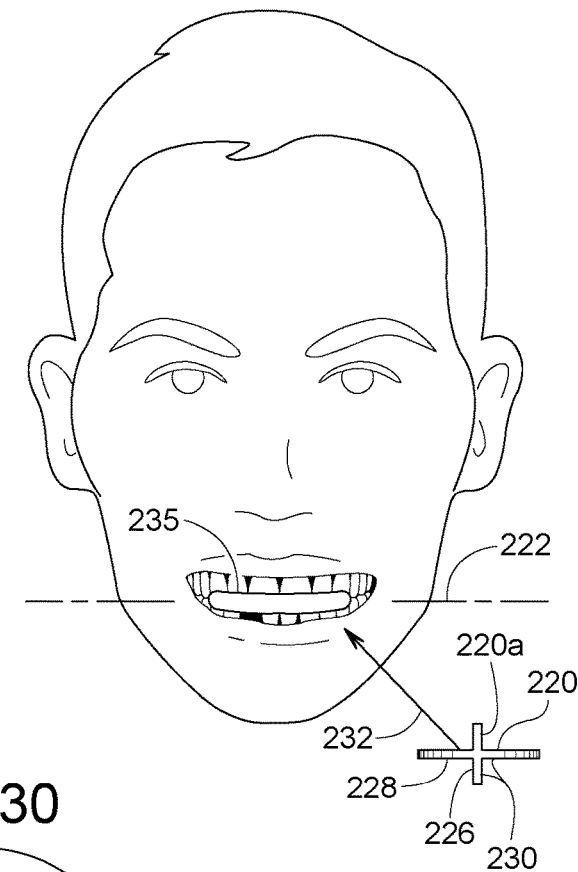
FIG. 29 is a front view similar to FIG. 28 but showing an example radiographic dental jig about to be attached to the patient via a wax bite impression, wherein the radiographic jig is constructed in accordance with the teachings disclosed herein.

FIG. 29 shows patient 10 having bitten into a wax bite impression 235. Wax bite impression 235 is a somewhat soft, compliant material that can be readily indented to record the patient's teeth marks. In FIG. 29, jig 220 is shown in the removed position, spaced apart from patient 10. Arrow 232 of FIG. 29 represents the process of attaching jig 220 to wax bite impression 235.

Figure 30:
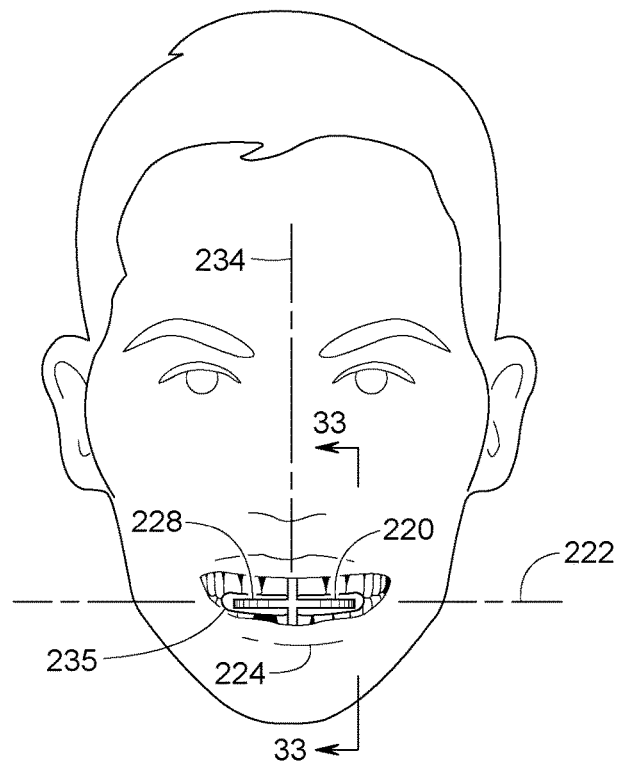
FIG. 30 is a front view similar to FIG. 29 but showing the jig in an attached position.

FIG. 30 shows jig 220 mounted to wax bite impression 235 in an attached position behind and engaging the patient's lip 224, while patient 10 is upright. When jig 220 is properly installed, post 226 is parallel to a midline 234 of patient 10. When the patient's head is perfectly upright, midline 234 is a vertical line halfway between the patient's eyes. Beam 228 is placed at the same elevation of the patient's incisal edge plane 222. Thus, midline 234 determines the proper left/right position of jig 220, and incisal edge plane 222 determines the jig's proper vertical position.

Figure 31:
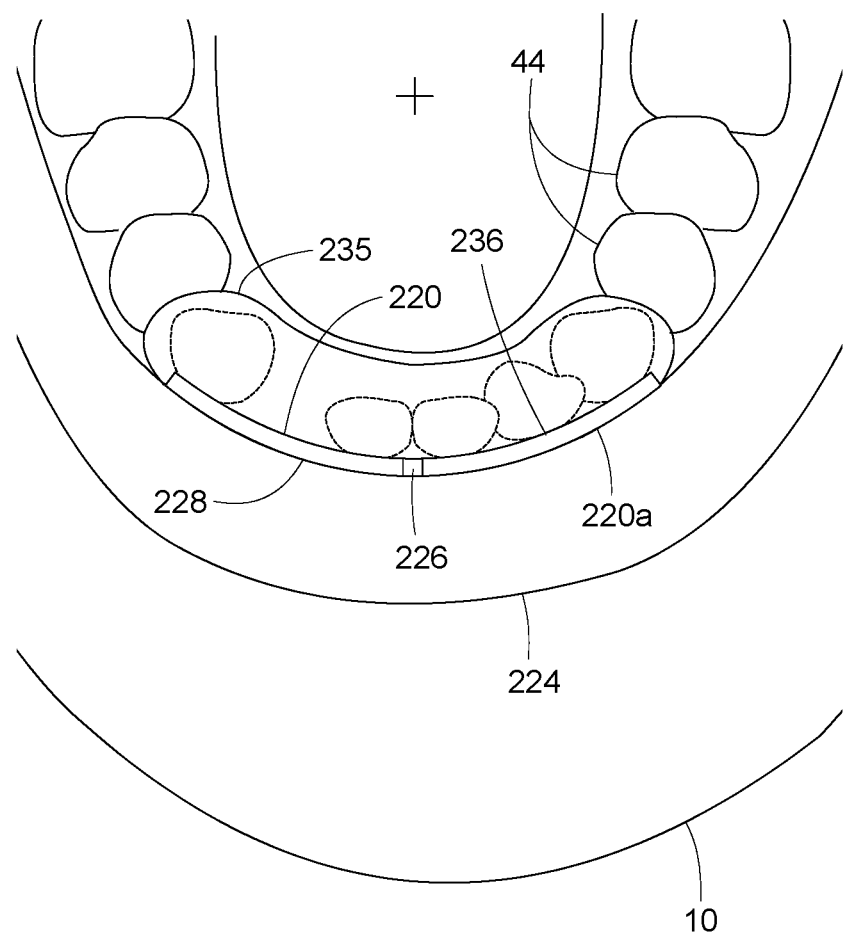
FIG. 31 is a cross-sectional view taken along line 31-31 of FIG. 33.

FIG. 31 is a top view looking down at the patient's lower set of teeth 44. In this view, FIG. 31 shows an inside surface 236 of the patient's lip 224 being used for determining the jig's proper front-to-back positioning. In examples where patient 10 has a significant amount of teeth, jig 220 is placed up against the lip's inside surface 236. In examples, where patient has few or no teeth to support lip 224, the front-to-back position of jig 220 is placed to define a desired target lip position to be achieved after dental restoration is completed.

Figure 32:
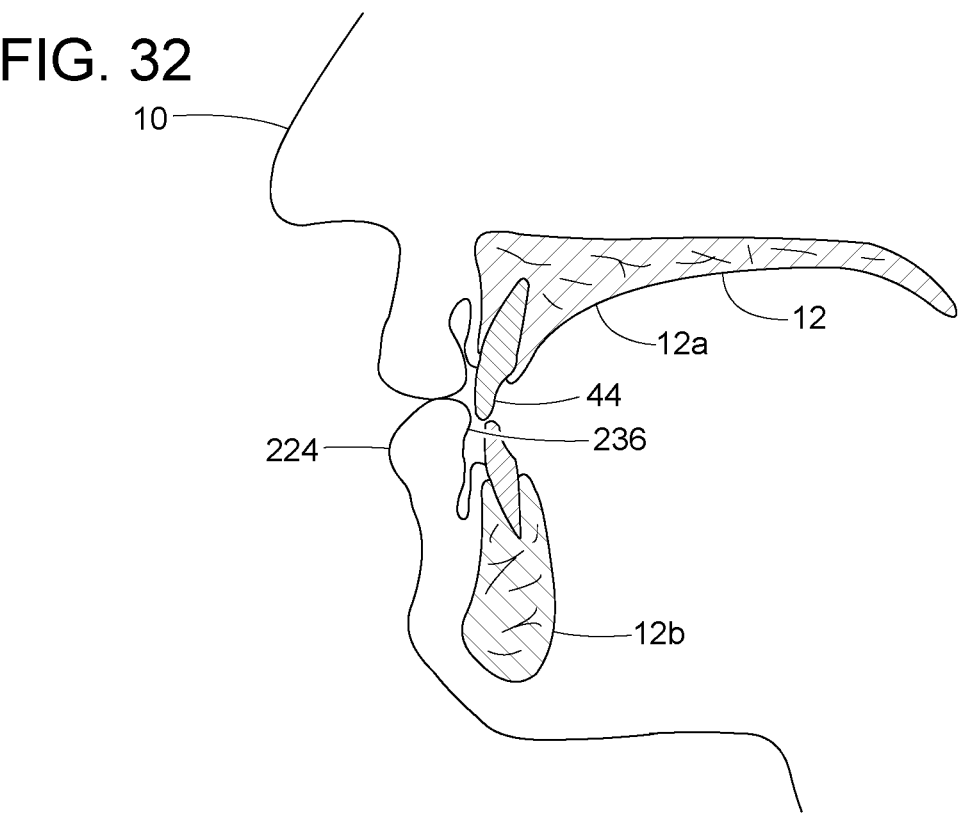
FIG. 32 is a cross-sectional view taken along line 32-32 of FIG. 28.
Figure 33:
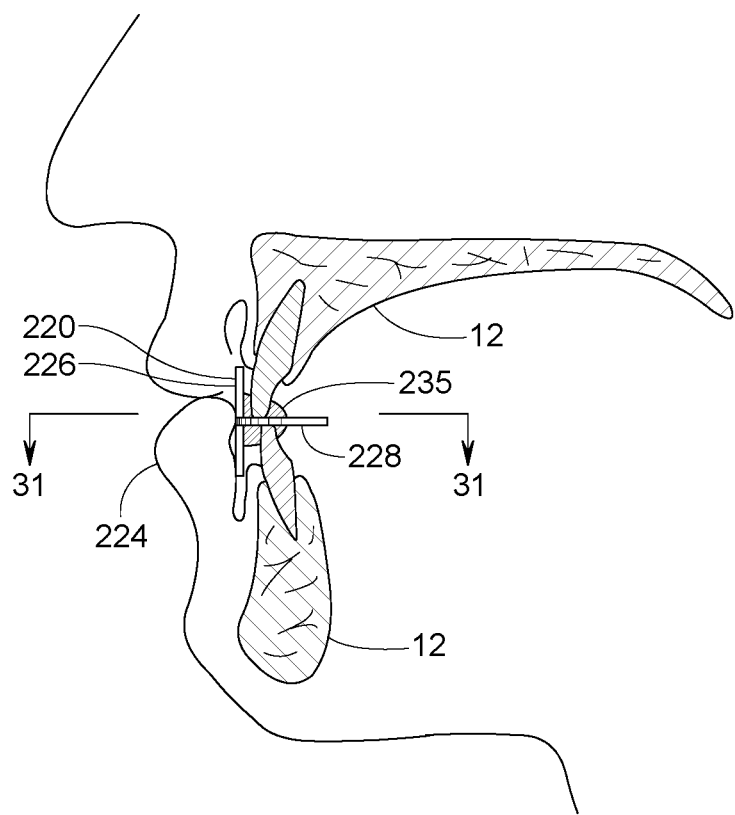
FIG. 33 is a cross-sectional view taken along line 33-33 of FIG. 30.

FIG. 32 is a cross-sectional side view taken along line 32-32 of FIG. 28. FIG. 33 is a cross-sectional side view taken along line 33-33 of FIG. 30. FIG. 33 shows wax bite impression 235 being further used as a fastener 238 for connecting jig 220 at a chosen attached position on the patient's jaws 12. In the attached position, jig 220 is attached either directly to the patient's jaw 12 (e.g., via an adhesive) or attached indirectly via an intermediate mounting structure, such as a denture, wax bite impression, or some other polymeric or metal device on the patient's jaw 12.

Denture 14 and wax bite impression 235 are some examples of a polymeric device. The term, "fastener" refers to any structure or material for attaching something, e.g., attaching jig 220. Some examples of fastener 238 include wax bite impression 235, an adhesive, a pin 240 (FIG. 45), a screw, a hook, a wire, and various combinations thereof, etc. Consequently, in some examples, wax bite impression 235 serves as both a fastener and a polymeric device to which jig 220 may be attached.

Figure 34:
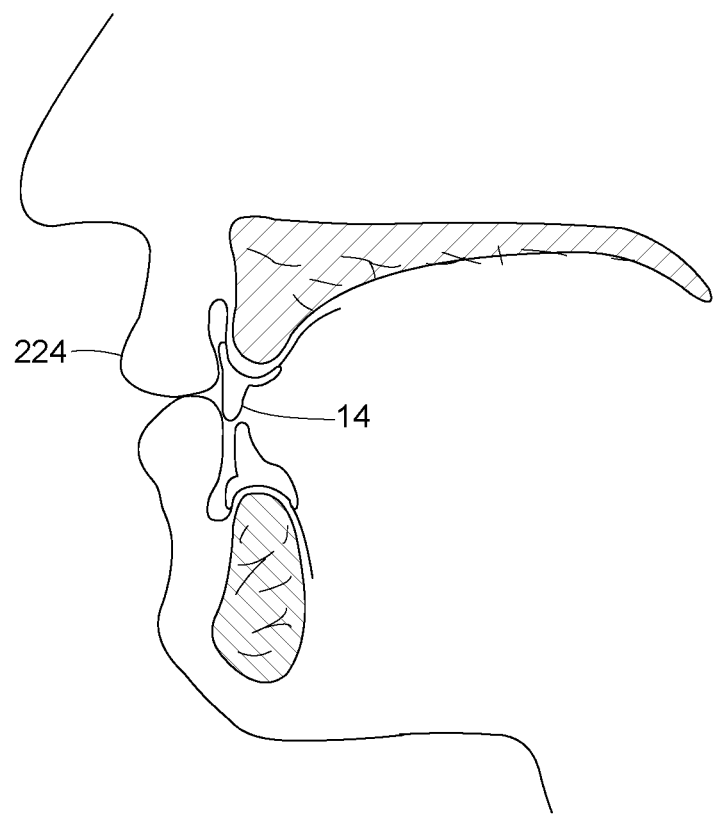
FIG. 34 is a cross-sectional view similar to FIG. 32 but showing a patient with dentures.
Figure 35:
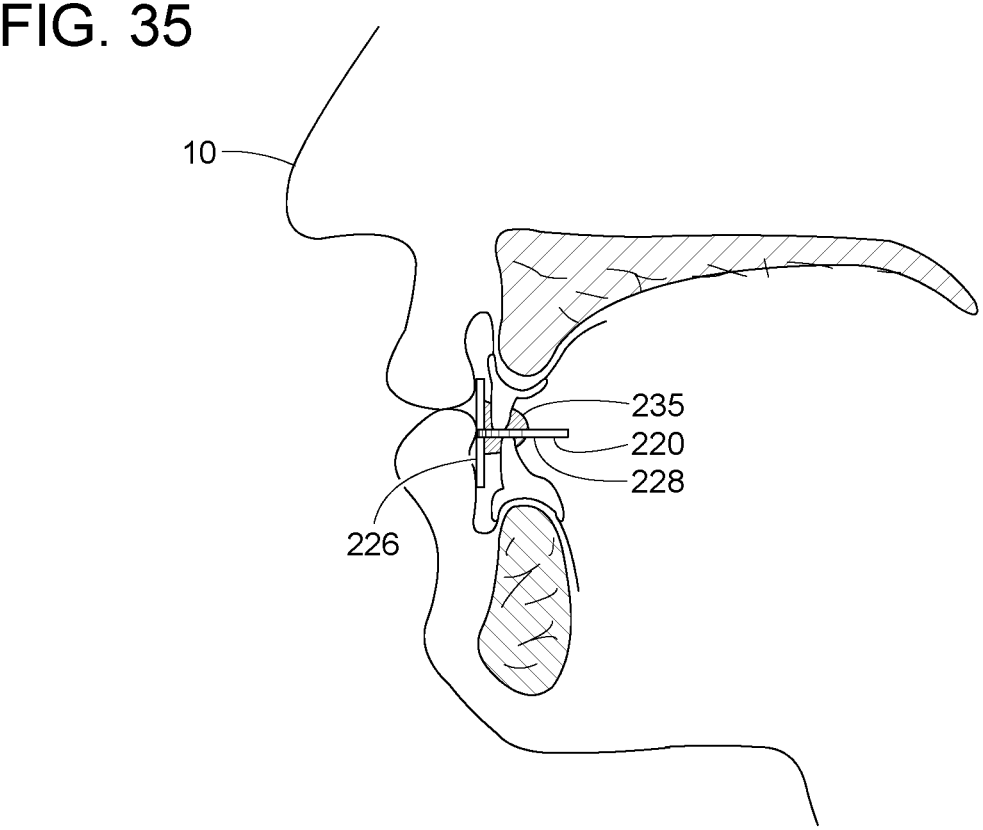
FIG. 35 is a cross-sectional view similar to FIG. 33 but showing the patient with dentures.

FIGS. 34 and 35 show patient 10 with upper and lower dentures 14. In this example, wax bite impression 235 is used for fastening jig 220 to dentures 14. In some examples, however, a pin is used as fastener 238 for attaching jig 220 directly to dentures 44 without relying on wax bite impression 235.

Figure 36:
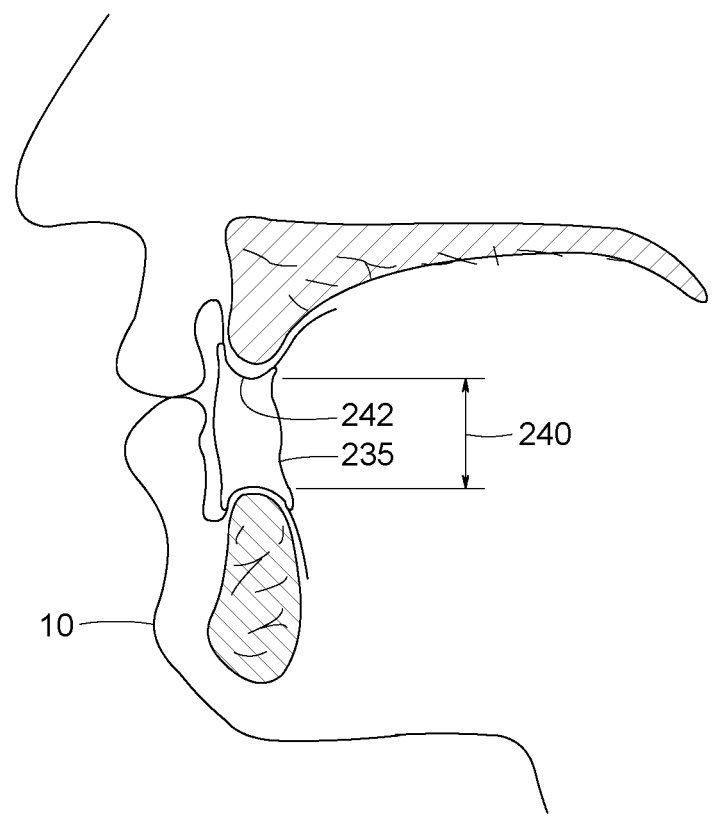
FIG. 36 is a cross-sectional view similar to FIG. 32 but showing a patient without any teeth.
Figure 37:
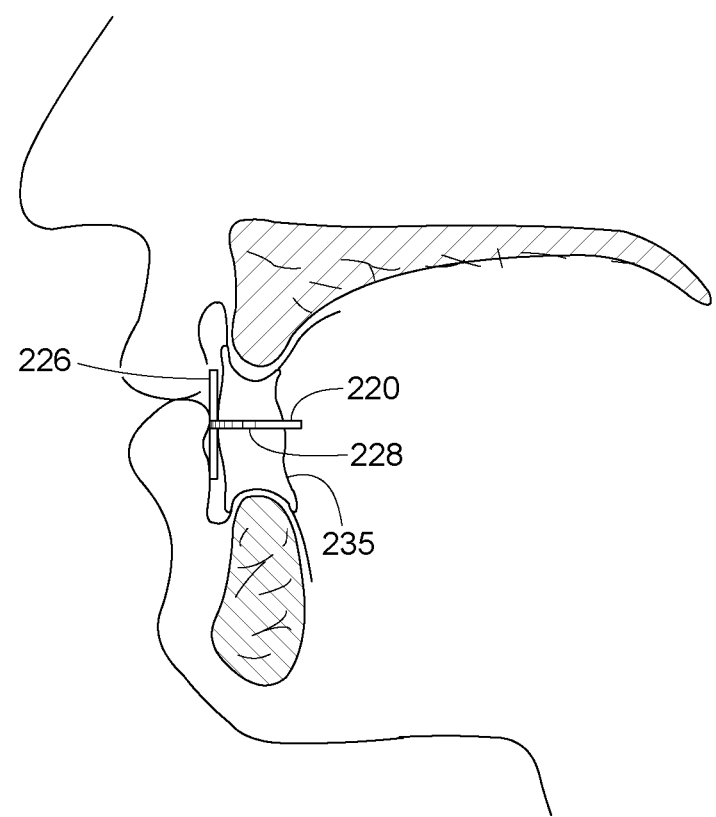
FIG. 37 is a cross-sectional view similar to FIG. 33 but showing the patient without any teeth.

FIGS. 36 and 37 show patient 10 without any teeth. In this example a relatively thick example of wax bite impression 235 is used for establishing a desired vertical gap 240 between the patient's upper and lower gums 242. The vertical gap 240 is to provide room for adding dentures or other prosthetic teeth. In this example, wax bite impression 235 is used for fastening jig 220 in position. FIG. 37 shows jig 220 affixed at a position to define how far forward the new prosthetic teeth should extend.

Figure 38:
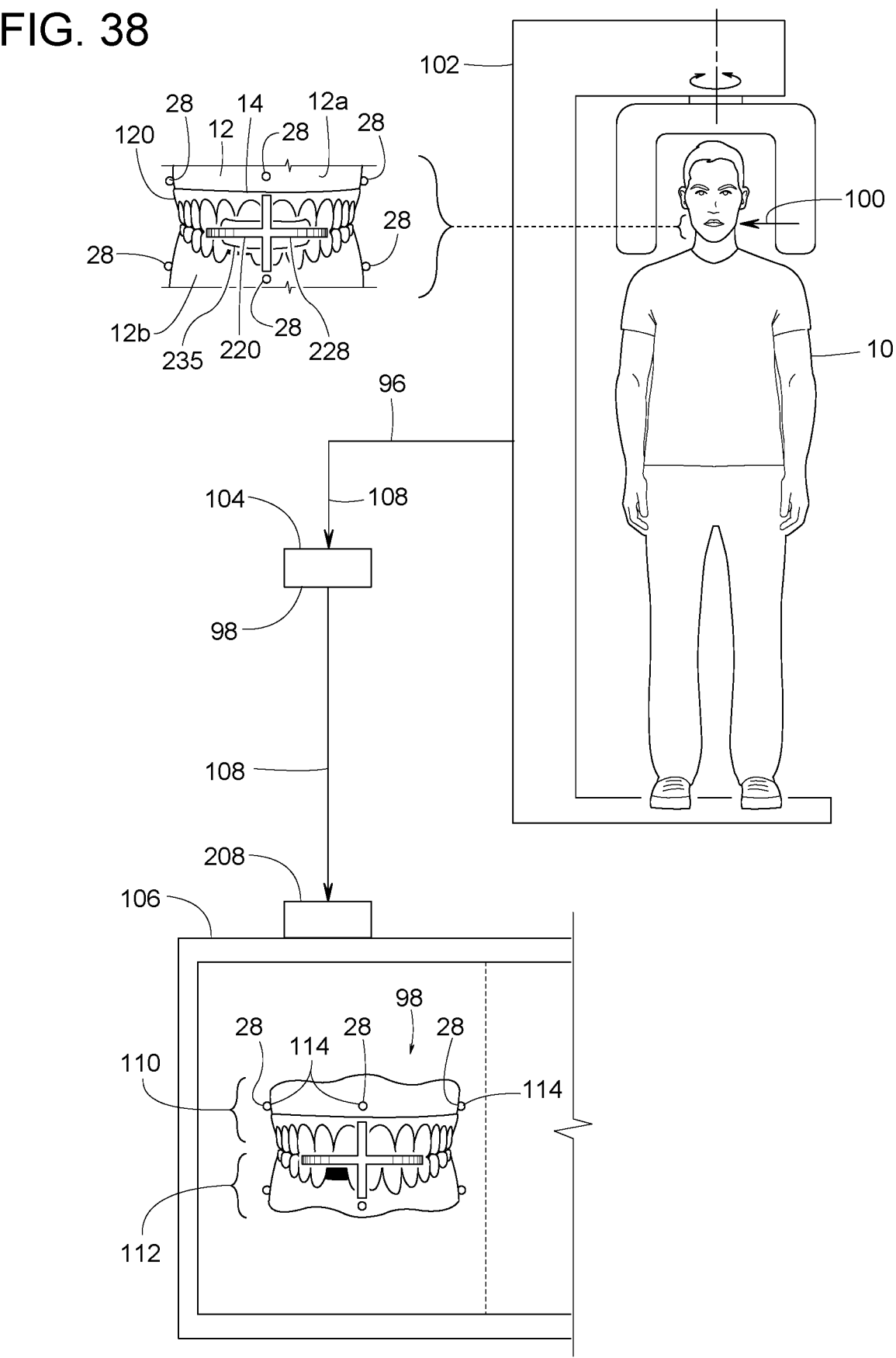
FIG. 38 is a schematic diagram similar to FIG. 10 but showing the additional use of the example jig.

FIG. 38 is similar to FIG. 10 but with the addition of jig 220. Also, in this particular examples, six fiducial markers 28 are installed. First scanning machine 102 radiographically scans patient 10 (including upper jaw 12a, lower jaw 72b, six fiducial markers 28, and jig 220) to create first scan result 98.

After creating first scan result 98, jig 220 is removed from patient 10. In some examples, cast models 134 and 136 are then made as illustrated in FIGS. 11-13. FIG. 14 illustrates scanner 144 or 140 creating second scan result 124 by scanning upper jaw 12a or a physical model 134 of upper jaw 12a. FIG. 14 also illustrates scanner 144 or 140 creating third scan result 126 by scanning lower jaw 12b or a physical model 136 of lower jaw 12b.

FIG. 39 shows the second scanned representation of the first jaw 158 and the second scanned representation of the second jaw 160 shifted relative to each other to correspond to first scanned representation of the first jaw 110 and the first scanned representation of the second jaw 112. The shifting process is achieved by aligning the fiducial markers 28 scanned by the first scanning machine 102 to the marker-shaped points 162 scanned by the second scanning machine 144 or 140. The shifting process creates digital jaw model 116.

FIG. 40. shows a filtered image 244 of jig 220 (image of the cross) and fiducial markers 28 derived from first scan result 98 created by first scanning machine 102. In the example shown in FIG. 40, a software opacity filter of first scan result 98 is adjusted such that fiducial markers 28 and jig 220 prominently emerge while less radiographically opaque tissue disappears.

In some examples, filtered image 244 of jig 220 and fiducial markers 28 are imported to create a composite image 246 that includes an image of the cross 230 (filtered image 244 of jig 220), image of the upper jaw (second scanned representation of first jaw 12a), and an image of the lower jaw (second scanned representation of second jaw 12b). Composite image 246 provides dental practitioner 168 with a digital 3D model (3-dimensional rendering) that can be virtually rotated in space to view orthogonally or in perspective. This enables dental practitioner 168 to design and plan reconstructive and/or orthodontic dental work that fits harmoniously with a predetermined incisal edge plane and desired lip location.

Figure 41:
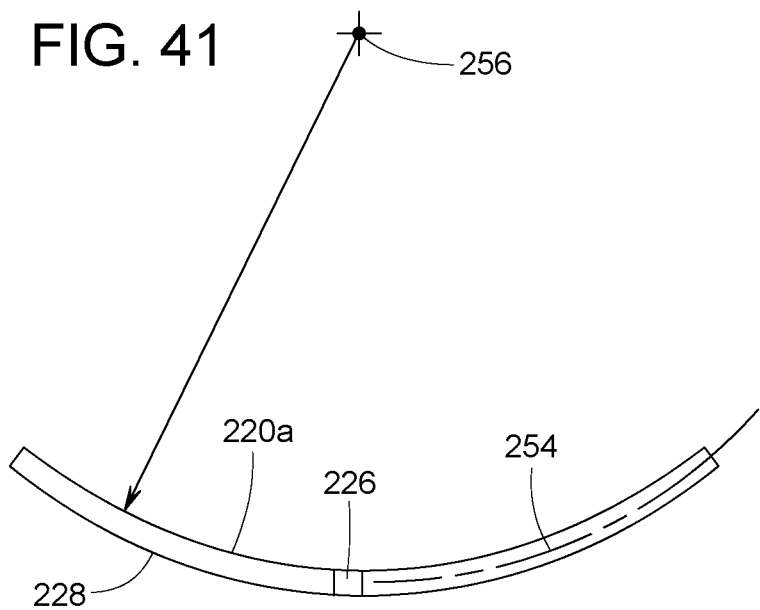
FIG. 41 is a top view of an example radiographic dental jig constructed in accordance with the teachings disclosed herein.
Figure 42:
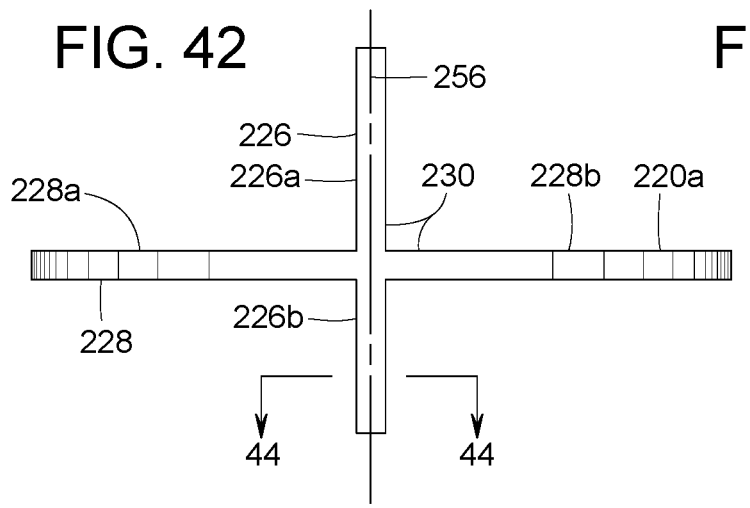
FIG. 42 is a front view of FIG. 41.
Figure 43:
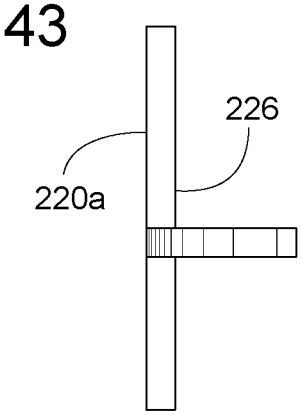
FIG. 43 is a right side view of FIG. 42.

In the example shown in FIGS. 41-43, FIG. 41 shows a top view of jig 220a, FIG. 42 shows a front view of jig 220a, and FIG. 43 shows a right side view of jig 220a. In this example, post 236 and beam 228 are plastic injection molded as a unit to provide cross 230 that is a seamless unitary piece.

Figure 44:
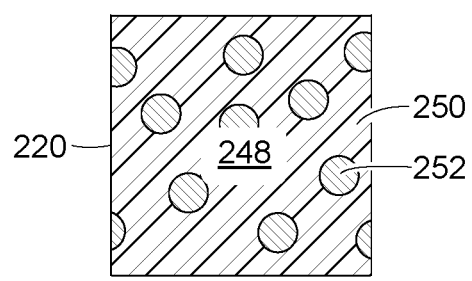
FIG. 44 is an enlarged cross-sectional view taken along line 44-44 of FIG. 42.

In some examples, jig 220a is plastic injection molded of a material that includes a mixture 248 of a polymeric binder 250 and a filler material 252, as shown in FIG. 44. Some examples of polymeric binder 250 include acrylic, polymethyl methacrylate (PMMA), polycarbonate, polystyrene, high-impact polystyrene (HIPS). Some examples of filler material 252 include barium, titanium, bismuth, tungsten, zirconium, and various compounds thereof. In some examples, filler material 252 includes barium sulfate, which can be finely mixed with polymeric binder 250.

In some examples, the proportions of binder 250 and filler material 252 may be important. Too much filler material 252 may create one or more problems, such as undesirable scatter in first scan result 98, structural weakness in jig 220, and/or difficulty in plastic injection molding the material. An insufficient amount of filler material 252 may render jig 220 so radiographically transparent that it becomes difficult to distinguish jig 220 from human tissue, thereby making it difficult or impossible to create filtered image 244, as shown in FIG. 40. Consequently, in some examples, filler material 252 is more than twice as dense as polymeric binder 250 and makes up 20% to 70% of the mixture's volume to provide mixture 248 with a density of 1.8 to 2.9 grams per cubic centimeter, which falls somewhere between the density of jaw bone and tooth enamel. Particularly favorable results are achieved when mixture 248 is mostly polymeric binder 250 by volume (i.e., polymeric binder 250 contributes at 50% of the mixture's volume).

In the illustrated example, beam 228 is longer than post 226 and defines a longitudinal centerline 254 that curves about an axis 256 that is substantially parallel to post 226. This may provide several benefits. One, the beam's curvature allows beam 228 to follow the normal curvature of a patient's mouth. Two, the beam's curvature helps provide natural looking back support for the lip of an edentulous patient. Three, when composite image 236 is viewed from the front, the appearance of beam 228 will indicate whether post 226 is vertical, leaning forward, or leaning back. Post 226 is vertical when beam 228, as viewed from the front, appears as a straight horizontal line.

Figure 45:
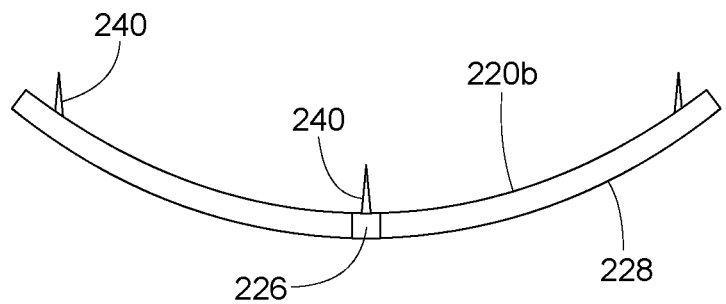
FIG. 45 is a top view similar to FIG. 41 but showing another example radiographic dental jig constructed in accordance with the teachings disclosed herein.

FIG. 45 shows jig 220b with one or more integral pins 240. Pins 240 may serves as fastener 238 for affixing jig 220b by poking into dentures 14 and/or into wax bite impression 235.

Post 226, in some examples, includes an upper portion 226a and a lower portion 226b, and beam 228 includes a left arm 228a and a right arm 228b. In some examples, upper portion 226a is longer than lower portion 226b to ensure that post 226 remains behind lip 224 when patient 10 smiles (e.g., FIG. 49).

Figure 46:
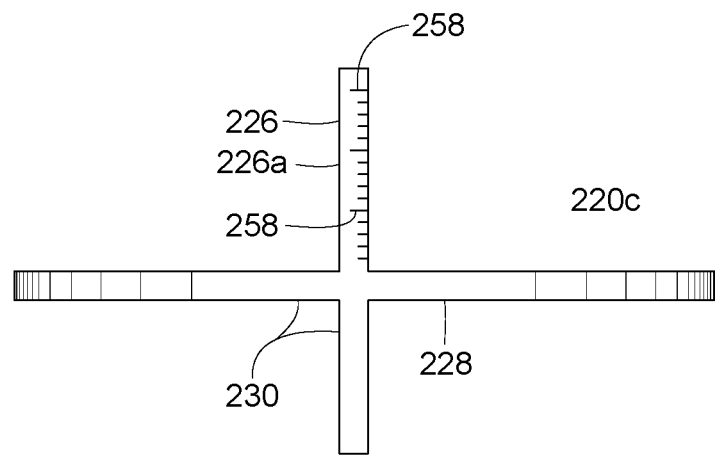
FIG. 46 is a front view similar to FIG. 42 but showing another example radiographic dental jig constructed in accordance with the teachings disclosed herein.
Figure 49:
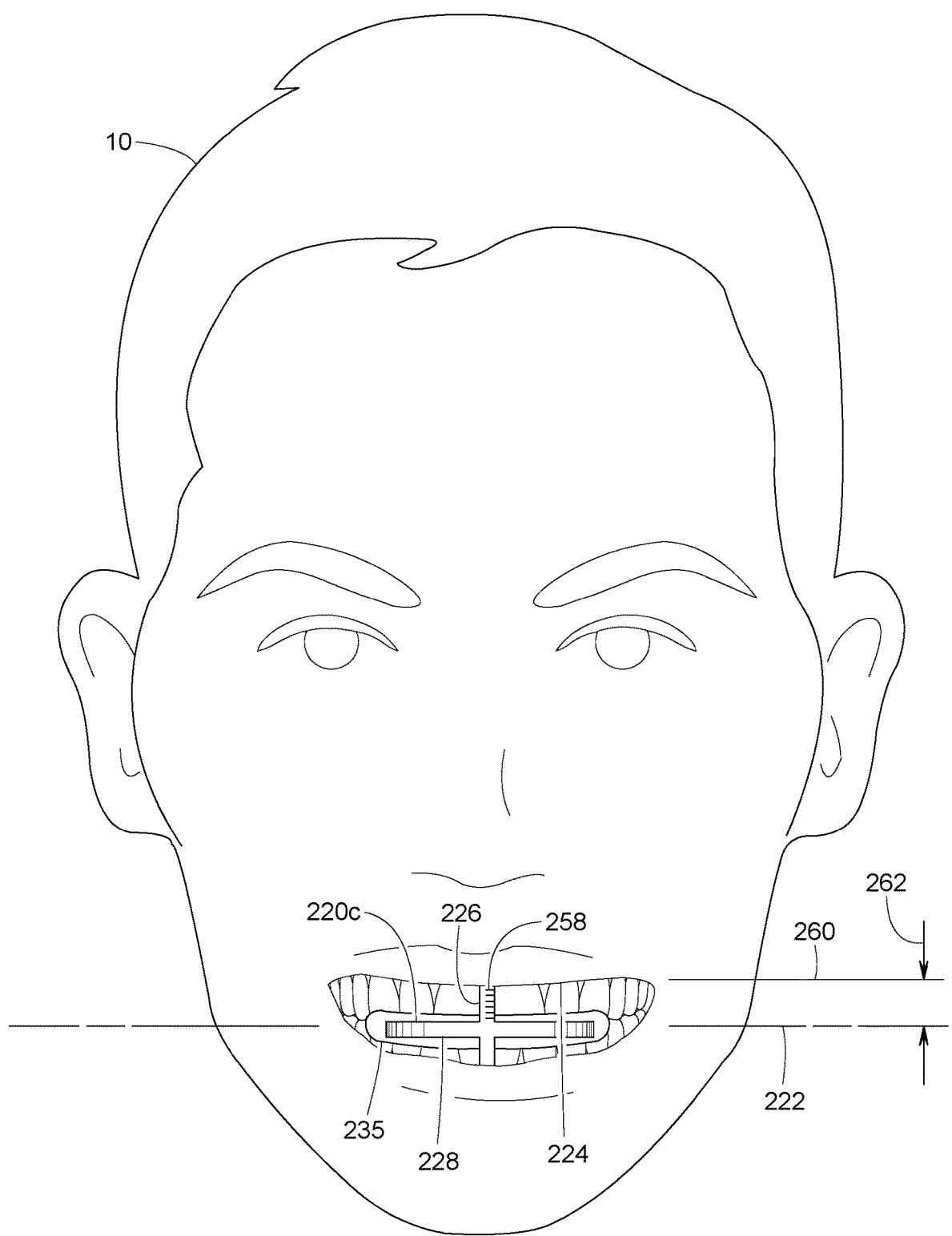
FIG. 49 is a front view similar to FIG. 30 but shown enlarged and with the jig of FIG. 46 in the attached position.

In some examples, as shown in FIG. 46, jig 220c includes a plurality of graduations 258 are on the post's upper portion 226a. Graduations 258 provide a measuring guide that helps dental practitioner 168 identify and record the patient's high smile line 260. High smile line 260 is the location of the patient's upper lip 224 relative to incisal edge plane 222 when patient 10 smiles fully. So, in some examples, graduations 258 identify dimension 262, as shown in FIG. 49.

Figure 47:
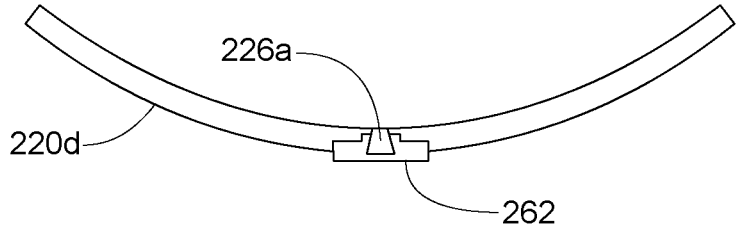
FIG. 47 is a top view similar to FIGS. 41 and 45 but showing another example radiographic dental jig constructed in accordance with the teachings disclosed herein.
Figure 48:
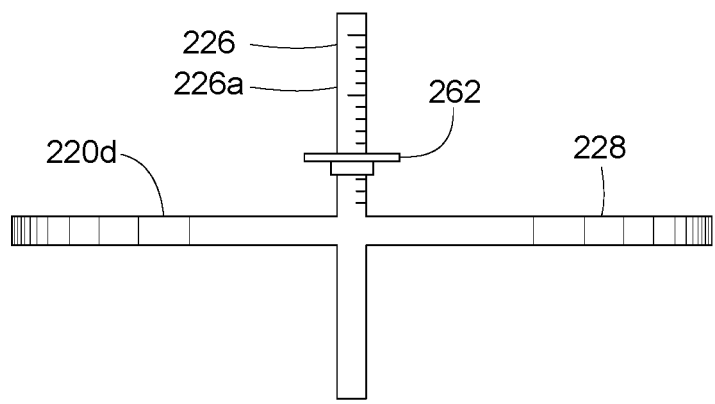
FIG. 48 is a front view of FIG. 47.

In the example shown in FIGS. 47 and 48, jig 220d includes a slider 262 that is attached in sliding relationship to the post's upper portion 226a. Slider 262 can help mark high smile line 260 with reference to post 226 (with or without graduations 258 thereon). A moderate amount of friction allows slider 262 to be readily slid along the post's upper portion 226a, yet the friction is sufficient to hold slider 262 in place when not forced to move.

In some examples, slider 262 is made of the same radiographic mixture 248 used in the rest of jig 220. So, when slider 262 is placed at high smile line 260, and left there, the location of high smile line 260 will appear on first scan result 98 and will later be imported and transferred onto composite image 246.

In some examples, jig 220 is used in a radiographic method for marking a reference position (e.g., FIGS. 31 and 33) of lip 224 of patient 10, including the patient's upper jaw 12a and lower jaw 12b. In such a method, FIGS. 41-43 illustrate providing post 226 that includes upper portion 226a and lower portion 226b. FIGS. 41-43 illustrate providing beam 228 that includes right arm 228a and left arm 228b, wherein beam 228 traverses post 226 to create cross 230, and post 226 is between right arm 228a and left arm 228b. Arrow 232 of FIG. 29 illustrates inserting cross 230 into the mouth of patient 10 such that when patient 10 is upright, cross 230 is behind lip 224 (FIG. 31), cross 230 is touching lip 224 (e.g., FIGS. 31 and 33), post 226 is substantially vertical (FIG. 30) with upper portion 226a being above lower portion 226b, and beam 228 is substantially horizontal. FIG. 38 illustrates creating, via first scanning machine 102, first scan result 98 by concurrently scanning 100 upper jaw 12a, lower jaw 12b, and cross 230. FIG. 14 illustrates creating, via second scanning machine 144 or 140, a second scan result 124 by scanning 142 or 138 at least one of upper jaw 12a and a physical model 134 of upper jaw 12a. FIG. 4 illustrates creating, via second scanning machine 144 or 140, a third scan result 126 by scanning 148 or 146 at least one of lower jaw 12b and a physical model 136 of lower jaw 12b, wherein first scanning machine 102 and second scanning machine 144 or 140 are two different machines. Arrows 264 and 266 of FIG. 40 represent creating composite image 246 that includes an image of cross 230, an image of upper jaw 12a, and an image of lower jaw 12b; wherein the image of the cross 230 is based on first scan result 98, the image of the upper jaw 12a is based on second scan result 124, and the image of the lower jaw 126 is based on the third scan result 126. Arrows 46, 48 and 50 of FIG. 4 and arrows 60, 62 and 64 of FIG. 6 represent attaching a plurality of fiducial markers 28 to at least one of upper jaw 12a and lower jaw 12b prior to creating first scan result 98, wherein the plurality of fiducial markers 28 are spaced apart from cross 230, the composite image 246 includes the image of the cross 230, the image of the upper jaw 12a, the image of the lower jaw 12b, and an image of the plurality of fiducial markers 28; wherein the image of the plurality of fiducial markers 28 is based on first scan result 98.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

The invention claimed is:

1. A radiographic dental jig for marking a reference position of a lip of a patient, the radiographic dental jig comprising:
   a post that includes a polymeric binder and a filler material, wherein the filler material is more than twice as dense as the polymeric binder; and
   a beam that includes the polymeric binder and the filler material, the beam traversing the post to create a cross, the cross having selectively an attached position and a removed position, the cross in the attached position being adjacent to the lip, the cross in the removed position being spaced apart from the patient, the post being vertically elongate when the cross is in the attached position while the patient is upright, and beam being horizontally elongate when the cross is in the attached position while the patient is upright.

2. The radiographic dental jig of claim 1, wherein the beam is longer than the post.

3. The radiographic dental jig of claim 1, wherein the beam defines a longitudinal centerline that curves about an axis that is substantially parallel the post.

4. The radiographic dental jig of claim 1, further comprising a plurality of graduations on the post.

5. A radiographic dental jig for marking a reference position of a lip of a patient, the radiographic dental jig comprising:
   a post that includes an upper portion and a lower portion; and
   a beam that includes a right arm and a left arm, the beam traversing the post to create a cross, the post being between the right arm and the left arm, the cross having selectively an attached position and a removed position, the cross in the attached position being situated adjacent to the lip, the cross in the removed position being spaced apart from the patient, the post being substantially vertical with the upper portion being above the lower portion when the cross is in the attached position while the patient is upright, the beam lying substantially horizontal when the cross is in the attached position while the patient is upright, the cross being a mixture of a polymeric binder and a filler material, the filler material being 20% to 70% of the mixture by volume, and the filler material being more than twice as dense as the polymeric binder.

6. The radiographic dental jig of claim 5, wherein the beam is longer than the post.

7. The radiographic dental jig of claim 5, wherein the cross is a seamless unitary piece.

8. The radiographic dental jig of claim 5, wherein the beam defines a longitudinal centerline that curves about an axis that is substantially parallel the post.

9. The radiographic dental jig of claim 5, further comprising a plurality of graduations on the post.

10. The radiographic dental jig of claim 5, further comprising a slider attached in sliding relationship to the upper portion of the post.

11. The radiographic dental jig of claim 5, further comprising a fastener for connecting the cross to a jaw of the patient so as to hold the cross at the attached position.

12. The radiographic dental jig of claim 11, wherein the fastener includes an adhesive.

13. The radiographic dental jig of claim 5, further comprising a fastener for connecting the cross to a polymeric device installed behind the lip of the patient so as to hold the cross at the attached position adjacent to the lip.

14. The radiographic dental jig of claim 13, wherein the fastener includes a pin.

15. The radiographic dental jig of claim 5, wherein the filler material includes barium, and the mixture has a density of 1.8 to 2.9 grams per cubic centimeter.

16. A radiographic dental method for marking a reference position of a lip of a patient that includes an upper jaw and a lower jaw, the radiographic dental method comprising:
   providing a post that includes an upper portion and a lower portion; and
   providing a beam that includes a right arm and a left arm, the beam traversing the post to create a cross, the post being between the right arm and the left arm;
   inserting the cross into the mouth of the patient such that when the patient is upright, the cross is adjacent to the lip, the cross is touching the lip, the post is substantially vertical with the upper portion being above the lower portion, and the beam is substantially horizontal;
   creating, via a first scanning machine, a first scan result by concurrently scanning the upper jaw, the lower jaw, and the cross;
   creating, via a second scanning machine, a second scan result by scanning at least one of the upper jaw and a physical model of the upper jaw;
   creating, via the second scanning machine, a third scan result by scanning at least one of the lower jaw and a physical model of the lower jaw, the first scanning machine and the second scanning machine being two different machines; and
   creating a composite image that includes an image of the cross, an image of the upper jaw, and an image of the lower jaw; wherein the image of the cross is based on the first scan result, the image of the upper jaw is based on the second scan result, and the image of the lower jaw is based on the third scan result.

17. The radiographic dental method of claim 16, further comprising attaching a plurality of fiducial markers to at least one of the upper jaw and the lower jaw prior to creating the first scan result, the plurality of fiducial markers being spaced apart from the cross, the composite image includes the image of the cross, the image of the upper jaw, the image of the lower jaw, and an image of the plurality of fiducial markers; wherein the image of the plurality of fiducial markers is based on the first scan result.

18. The radiographic dental method of claim 16, wherein the beam is longer than the post.

19. The radiographic dental method of claim 16, wherein the beam defines a longitudinal centerline that curves about an axis that is substantially parallel the post.

20. The radiographic dental method of claim 16, further comprising a plurality of graduations on the post.

* * * * *